(12) United States Patent
Sankai

(10) Patent No.: US 8,425,436 B2
(45) Date of Patent: Apr. 23, 2013

(54) MOTION ASSISTIVE DEVICE AND MAINTENANCE MANAGEMENT SYSTEM FOR MOTION ASSISTIVE DEVICE

(75) Inventor: Yoshiyuki Sankai, Tsukuba (JP)

(73) Assignee: University of Tsukuba, Tsukuba-Shi, Ibaraki (JP)

( * ) Notice: Subject to any disclaimer, the term of this patent is extended or adjusted under 35 U.S.C. 154(b) by 833 days.

(21) Appl. No.: 12/311,589

(22) PCT Filed: Sep. 27, 2007

(86) PCT No.: PCT/JP2007/068856
§ 371 (c)(1), (2), (4) Date: Nov. 9, 2009

(87) PCT Pub. No.: WO2008/041614
PCT Pub. Date: Apr. 10, 2008

(65) Prior Publication Data
US 2010/0063601 A1 Mar. 11, 2010

(30) Foreign Application Priority Data

Oct. 3, 2006 (JP) ................................ 2006-272223
Sep. 19, 2007 (JP) ................................ 2007-242648

(51) Int. Cl.
| | |
|---|---|
| *A61H 1/00* | (2006.01) |
| *H02K 29/06* | (2006.01) |
| *H02P 7/00* | (2006.01) |
| *G05B 19/04* | (2006.01) |

(52) U.S. Cl.
USPC ........ 601/5; 318/400.39; 318/471; 318/568.2

(58) Field of Classification Search ................ 601/5, 23, 601/33–35, 84, DIG. 21, DIG. 22, DIG. 232; 310/68 B; 318/471, 400.08, 400.39, 400.4; 250/231.13, 231.14, 231.18, 578.1; 356/3.1, 356/4.01, 139.09, 499, 616; 324/765.01
See application file for complete search history.

(56) References Cited

U.S. PATENT DOCUMENTS 4,525,763 A * 6/1985 Hardy et al. .................... 361/24
5,216,245 A * 6/1993 Keegan et al. ........... 250/227.23
(Continued)

FOREIGN PATENT DOCUMENTS

| EP | 0 794 475 A1 | 9/1997 |
| JP | 62-218094 A | 9/1987 |

(Continued)

OTHER PUBLICATIONS

Patent Abstracts of Japan of JP 9-14941 dated Jan. 17, 1997.

(Continued)

*Primary Examiner* — Justine Yu
*Assistant Examiner* — Christopher Miller
(74) *Attorney, Agent, or Firm* — Ladas & Parry LLP

(57) ABSTRACT

An operating status of a motor in a drive unit is analyzed to extend the life of the motor. A wearable motion assistive device 1 includes a shoulder joint mechanism 5 and an elbow joint mechanism 6 for aiding a movement of the shoulder joint and the elbow joint, and a control unit 100 having a control circuit for controlling drive units 11 for the shoulder and elbow joint mechanisms 5 and 6. The control unit 100 controls the drive units 11 based on a physical quantity and a biosignal detected by an angle sensor, a torque sensor, and a biosignal detecting sensor. A controller in the drive unit 11 includes a motor monitoring unit for monitoring an operational status of the motor, and a motor control unit for limiting a drive signal supplied to the motor based on a monitoring result provided by the motor monitoring unit, in order to prevent an overload state of the motor.

17 Claims, 25 Drawing Sheets

U.S. PATENT DOCUMENTS

| | | | |
|---|---|---|---|
| 5,337,737 A * | 8/1994 | Rubin et al. | 601/33 |
| 6,552,329 B2 * | 4/2003 | Haas et al. | 250/231.13 |
| 6,865,513 B2 * | 3/2005 | Ushiku et al. | 702/184 |
| 2001/0026134 A1 * | 10/2001 | Fukumoto et al. | 318/430 |
| 2004/0225384 A1 | 11/2004 | Onishi et al. | |
| 2004/0263342 A1 | 12/2004 | Matlock et al. | |
| 2005/0033557 A1 * | 2/2005 | House et al. | 702/184 |
| 2005/0051717 A1 * | 3/2005 | Akahane | 250/231.13 |
| 2005/0162113 A1 * | 7/2005 | Fujimoto et al. | 318/434 |
| 2005/0286181 A1 | 12/2005 | Ochiai | |
| 2006/0050285 A1 * | 3/2006 | Weller | 356/616 |
| 2006/0103337 A1 * | 5/2006 | Kasbarian et al. | 318/434 |
| 2006/0211956 A1 | 9/2006 | Sankai | |

FOREIGN PATENT DOCUMENTS

| | | | |
|---|---|---|---|
| JP | 3-222692 A | | 10/1991 |
| JP | 5-254454 | | 10/1993 |
| JP | 05254454 A | * | 10/1993 |
| JP | 9-14941 | | 1/1997 |
| JP | 9-91025 A | | 4/1997 |
| JP | 10-180662 A | | 7/1998 |
| JP | 2001-292586 A | | 10/2001 |
| JP | 2003-99114 | | 4/2003 |
| JP | 2005-25751 | | 1/2005 |
| JP | 2005-95561 | | 4/2005 |
| JP | 2006-14495 | | 1/2006 |
| JP | 2006-72836 | | 3/2006 |
| WO | 01/73215 | | 10/2001 |

OTHER PUBLICATIONS

Patent Abstracts of Japan of JP 2003-99114 dated Apr. 4, 2003.
Patent Abstracts of Japan of JP 2006-72836 Mar. 16, 2006.
Patent Abstracts of Japan of JP 2005-25751 dated Jan. 27, 2005.
Office Action dated Jul. 24, 2012 for Application No. JP 2007-242648 with English translation.
Patent Abstracts of Japan English abstract of JP 3-222692 A.
Patent Abstracts of Japan English abstract of JP 9-91025 A.
Patent Abstracts of Japan English abstract of JP 10-180662 A.
English abstract of JP 62-218094 A.
Patent Abstracts of Japan English abstract of JP 2001-292586 A.

* cited by examiner

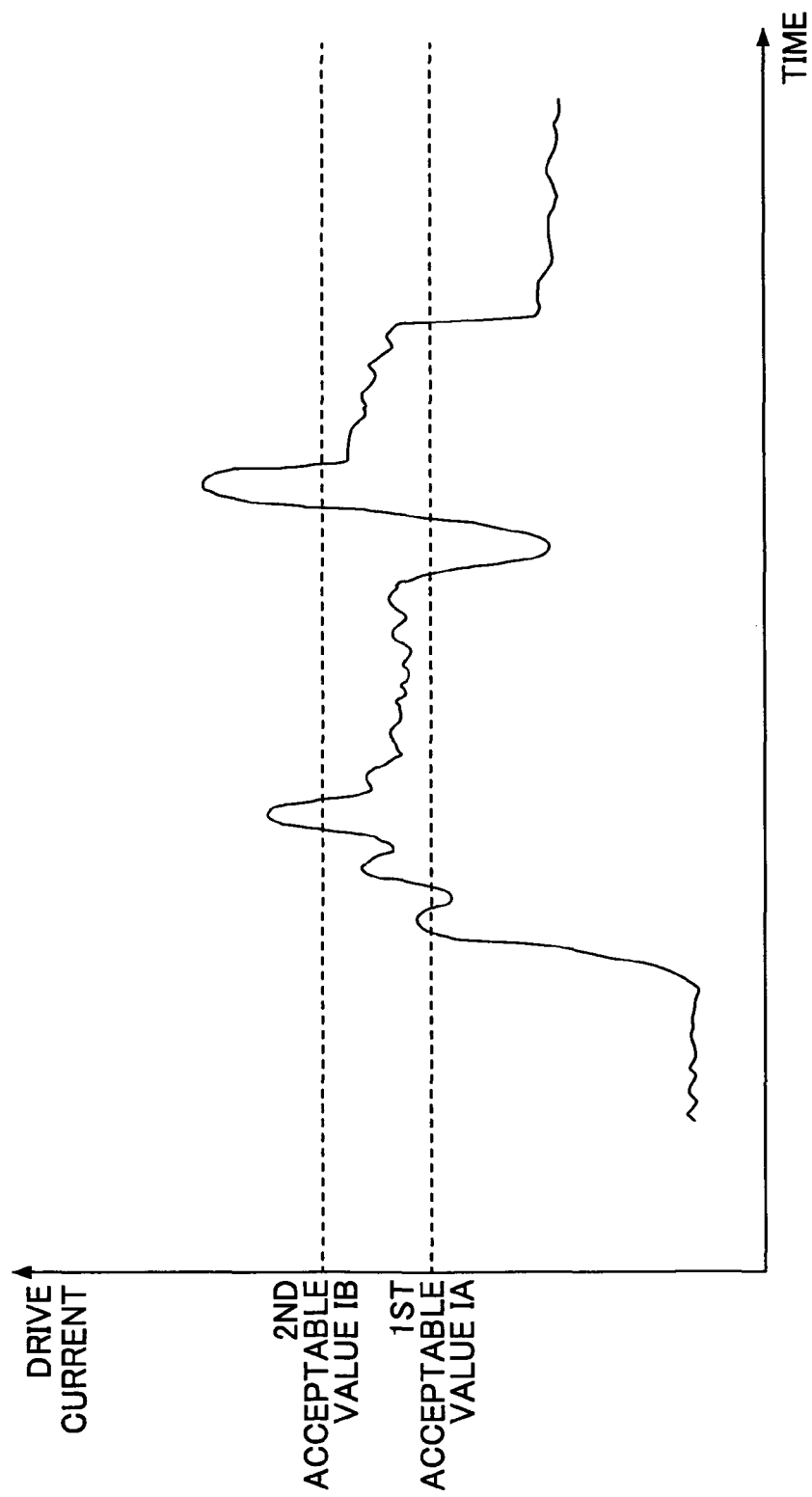

MOTION ASSISTIVE DEVICE AND MAINTENANCE MANAGEMENT SYSTEM FOR MOTION ASSISTIVE DEVICE

TECHNICAL FIELD

The present invention relates to motion assistive devices and maintenance management systems for motion assistive devices. In particular, the present invention relates to a motion assistive device for managing an operational status of a drive unit and a maintenance management system for such a motion assistive device.

BACKGROUND ART

In recent years, various aiding apparatuses have been developed for aiding the movements of the physically disabled or the elderly persons. For example, Patent Document 1 discloses a wearable motion assistive device that has a joint that mutually rotatably connects plural arms. An actuator rotates one arm relative to another, and a rotation angle of the arm is detected by an angle sensor.

In another example, Patent Document 2 discloses a rotation angle detecting apparatus in which a detection element is disposed in a radial direction of a rotating axle. In this rotation angle detecting apparatus, a reflective tape is spirally fixed on a circumferential surface of the rotating axle. Light is projected in a direction intersecting the reflective tape, and reflected light from the reflective tape is captured with the detection element. Based on the amount of displacement in the incident position of the reflected light from the reflective tape as the rotating axle is rotated, the rotation angle of the rotating axle is detected.

In another example, Patent Document 3 discloses a monitoring system for monitoring an operating status of a motor. In this monitoring system, plural sensors are used to monitor the operating status of the motor. If data regarding the operating status exceeds a threshold, an alert is displayed.

Patent Document 1: Japanese Laid-Open Patent Application No. 2005-95561
Patent Document 2: Japanese Laid-Open Patent Application No. 9-14941
Patent Document 3: Japanese Laid-Open Patent Application No. 2005-25751

DISCLOSURE OF THE INVENTION

Problems to be Solved by the Invention

However, in the aforementioned motion assistive device, there are several possible problems. For example, the motor may fail after a long period of use of a drive unit generating a driving force. The drive unit may not be able to generate the same driving force in response to the input of the same drive signal due to aging. Further, the motor may be subjected to excess load and overheat.

In some wearers of the motion assistive device, the drive unit for driving a joint is embedded inside the body of the wearer. In this case, it is difficult to examine the operating status of the motor externally. In addition, when some trouble is suspected in the motor, the motor cannot be easily repaired.

It is therefore an object of the present invention to detect a situation where a motor may fail or excess load is applied to the motor, and control the driving of the motor depending on the detected situation.

Means of Solving the Problems

In order to solve the aforementioned problems, the present invention provides the following:

(1) A motion assistive device comprising a drive unit configured to aid or execute an operation of a joint, and a control unit configured to control the drive unit, the drive unit including:
a motor configured to provide an inputted driving force; and
a circuit board on which a controller is mounted, the controller producing a drive signal supplied to the motor based on a control signal sent from the control unit,
wherein the controller includes:
a motor monitoring unit configured to monitor an operational status of the motor; and
a motor control unit configured to limit the drive signal supplied to the motor based on a result of monitoring by the motor monitoring unit in order to prevent an overload state of the motor.

(2) The motion assistive device according to one embodiment further comprises:
a physical quantity detecting unit configured to detect a physical quantity concerning the operation of the joint; and
a biosignal detecting unit configured to detect a biosignal that is generated when the joint is moved,
wherein the control unit controls the drive unit based on the physical quantity detected by the physical quantity detecting unit and the biosignal detected by the biosignal detecting unit.

(3) The motion assistive device according to one embodiment, wherein the motor control unit includes:
a determination unit configured to determine whether a total integrated value of electric current inputted to the motor exceeds a preset threshold; and
a motor control unit configured to decrease the drive signal supplied to the motor gradually at a predetermined rate when the determination unit determines that the total integrated value of the electric current exceeds the preset threshold.

(4) The motion assistive device according to one embodiment, wherein the motor control unit includes:
a determination unit configured to determine whether a temperature of the circuit board exceeds a preset threshold; and
a motor limiting unit configured to gradually decrease the drive signal supplied to the motor at a predetermined rate when the determination unit determines that the temperature of the control unit exceeds the preset threshold.

(5) The motion assistive device according to one embodiment, wherein the motor control unit includes:
a determination unit configured to determine whether a temperature of the motor exceeds a preset threshold; and
a motor limiting unit configured to gradually decrease the drive signal supplied to the motor at a predetermined rate when the determination unit determines that the temperature of the control unit exceeds the preset threshold.

(6) A motion assistive device comprising a drive unit configured to aid or execute an operation of a joint, and a control unit configured to control the drive unit, the drive unit including:
a motor configured to provide an inputted driving force; and
a controller configured to produce a drive signal supplied to the motor based on a control signal sent from the control unit,
wherein the controller includes:
a motor monitoring unit configured to calculate a remaining lifetime of the motor by subtracting a total operation time of the motor from a lifetime of the motor; and
a motor control unit configured to gradually decrease the drive signal supplied to the motor at a predetermined rate when the remaining lifetime of the motor calculated by the motor monitoring unit reaches a preset value.

(7) The motion assistive device according to one embodiment, wherein the controller includes:
a storage unit configured to store a first acceptable value of the electric current supplied to the motor, and a second acceptable value that is higher than the first acceptable value;
a calculating unit configured to integrate an electric current value in excess of the first acceptable value; and
a motor limiting unit configured to gradually decrease the value of the electric current supplied to the motor at a predetermined rate when an integrated value calculated by the calculating unit exceeds the threshold.

(8) The motion assistive device according to one embodiment, wherein the motor control unit is configured to gradually decrease the value of the electric current supplied to the motor to or below the first acceptable value when the value of the electric current supplied to the motor exceeds the second acceptable value.

(9) The motion assistive device according to one embodiment, wherein the drive unit includes:
a motor;
a case housing the motor;
a rotating body housed within the case and having a circumferential surface that rotates relative to the case when the motor is driven;
a fluorescent band disposed on and extending along the circumferential surface of the rotating body while inclined with respect to a circumferential direction of the rotating body;
a light-emitting portion configured to irradiate the fluorescent band with light;
a detecting unit that remains stationary relative to the case and includes a light-receiving surface opposite the fluorescent band, the detecting unit being configured to detect position information about the fluorescent band in an axial direction of the rotating body by receiving light emitted by the fluorescent band; and
a calculating unit configured to calculate a relative rotation angle between the case and the rotating body based on the position information about the fluorescent band detected by the detecting unit.

(10) The motion assistive device according to one embodiment, wherein the light-emitting portion is configured to turn on and off alternately when irradiating the fluorescent band with light, and
the detecting unit is configured to detect the position information about the fluorescent band by receiving light emitted by the fluorescent band when the light-emitting portion is turned off.

(11) The motion assistive device according to one embodiment, wherein the drive unit includes:
a motor;
a case housing the motor;
a rotating body housed within the case and having a circumferential surface that rotates relative to the case when the motor is driven;
a reflecting band disposed on and extending along the circumferential surface of the rotating body while inclined with respect to a circumferential direction of the rotating body,
a first light-emitting portion configured to irradiate the reflecting band with light;
a second light-emitting portion disposed away from the first light-emitting portion in an axial direction of the rotating body and configured to irradiate the reflecting band with light;
a detecting unit that remains stationary relative to the case and includes a light-receiving surface opposite the reflecting band, the detecting unit being configured to detect position information about the reflecting band in the axial direction of the rotating body by receiving light from the first light-emitting portion that is reflected by the reflecting band and light from the second light-emitting portion that is reflected by the reflecting band; and
a calculating unit configured to calculate a relative rotation angle between the case and the rotating body based on the position information about the reflecting band detected by the detecting unit.

(12) The motion assistive device according to one embodiment, wherein the first light-emitting portion and the second light-emitting portion are configured to turn on alternately, and
the detecting unit detects the position information about the reflecting band based on a distribution of reflected light that is detected when the first light-emitting portion is turned on and a distribution of reflected light that is detected when the second light-emitting portion is turned on.

(13) The motion assistive device according to one embodiment, wherein the rotating body comprises a gear case in which one or plural gears are housed.

(14) The motion assistive device according to one embodiment, including a slit member disposed between the detecting unit and the rotating body and having a slit formed in the axial direction of the rotating body.

(15) The motion assistive device according to one embodiment, wherein the drive unit includes a communication unit configured to transmit information including history information about a drive status of the motor.

(16) A maintenance management system for a motion assistive device, the system comprising:
the motion assistive device according to one embodiment;
a receiver unit provided at a center for managing an operational status of the motion assistive device and configured to receive the history information about the drive status of the motor that the drive unit transmits via the communication unit and a communication network;
a database configured to store the history information about the drive status of the motor that is inputted via the receiver unit;
an analyzing unit configured to generate information about a lifetime of the drive unit or a presence or an absence of an overload state in the drive unit by analyzing the history information stored in the database; and
a transmitter unit configured to transmit maintenance information to the drive unit when it is determined that the motor needs maintenance based on a result of analysis by the analyzing unit.

EFFECTS OF THE INVENTION

In accordance with the present invention, the drive unit includes a motor monitoring unit configured to monitor an operational status of the motor, and a motor control unit configured to limit a drive signal fed to the motor based on a monitoring result provided by the motor monitoring unit, in order to prevent an overload state of the motor. Thus, the problems caused by the forcible driving of the motor when the motor performance is lowered, or by the overheating of the motor or the circuit board can be prevented. Thus, when it is likely that the motor will be put in an overload state if a normal drive signal is fed to the motor when the performance of the motor is dropped due to aging or the like, the drive signal is gradually decreased so that the driving force of the motor can be reduced, thereby extending the life of the motor. In particular, when the drive unit is embedded within the body of the wearer, the motor cannot be replaced easily. In this case, the burden on the wearer can be reduced by extending the life of the motor.

In accordance with the present invention, when the remaining lifetime of the motor has reached a preset value, the drive signal fed to the motor is gradually decreased at a predetermined rate. Thus a sudden drop in motor performance in response to a drive signal can be prevented, thereby preventing a sudden stop of the motor and the resultant total loss of the motor driving force against the will of the wearer.

In accordance with the present invention, history information about the drive status of the motor that is transmitted from the drive unit via a communication unit and a communication network is stored in a database at a center for managing the operational status of the motion assistive device. The history information stored in the database is analyzed based on information about the life of the drive unit or the presence or absence of an overload state. Depending on an analysis result, maintenance information is transmitted to the drive unit. Thus, whether the drive unit is normal can be analyzed constantly. In addition, should some form of abnormality develop in the drive unit, an alert is issued immediately to notify the wearer.

BRIEF DESCRIPTION OF THE DRAWINGS

FIG. 12B shows a graph plotting drive current for a motor 31 versus time;

Figure 1:
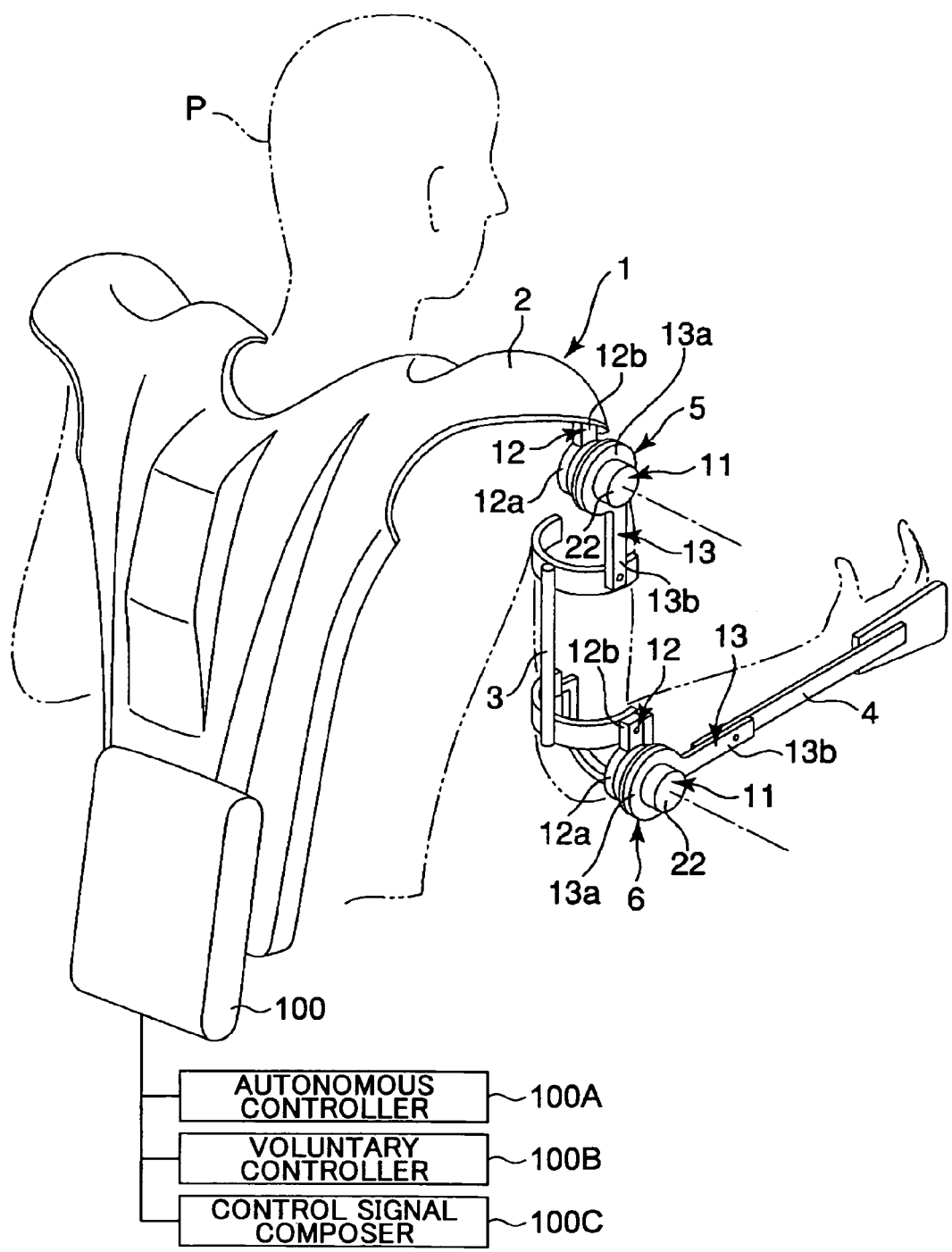
FIG. 1 shows a perspective view of a wearable motion assistive device according to a first embodiment of the present invention.

DESCRIPTION OF THE REFERENCE NUMERALS 1, 91, 101, 111, 121 Wearable motion assistive device
2 Body member
3 Upper arm member
4 Forearm member
5 Shoulder joint mechanism
6 Elbow joint mechanism
11, 92, 102, 112, 122, 290, 550 Drive unit
23, 24 Flange member
31 Motor
34 Inner case
35 Outer case
41 Circuit board
45 Controller
51, 93, 103, 113, 123 Rotation angle detecting unit
52 Temperature detecting unit
53 Distortion/vibration detecting unit
54 Current information detecting unit
61, 94 Detected member
62, 95, 96 Light-emitting portion
63 Position detecting unit
63a Light-receiving surface
64 Angle calculating unit
66 Slit member
68 Main body
69 Fluorescent band
83 Communication network
84 Information management apparatus
85 Communication unit
86 Storage unit
87 Analyzing unit
88 Database
97 Reflecting band
100 Control unit
200, 500 Embedded motion assistive device

BEST MODE OF CARRYING OUT THE INVENTION

Wearable motion assistive devices and drive units according to various embodiments of the present invention are described with reference to the drawings.

FIGS. 1 through 13 show a wearable motion assistive device 1 according to a first embodiment of the present invention. FIG. 1 shows, as a representative example, an upper-right portion of the wearable motion assistive device 1 corresponding to the right arm portion of a wearer P. The wearable motion assistive device 1 includes a body member 2, an upper arm member 3, and a forearm member 4. The body member 2 is attached to the body of the wearer P. The upper arm member 3 is attached to and extends along the upper arm of the wearer P. The forearm member 4 is attached to and extends along the forearm of the wearer P.

The wearable motion assistive device 1 includes an angle sensor (physical quantity detecting unit) for detecting a physical quantity regarding a movement of a joint, such as the shoulder or elbow joint; a biological sensor (biosignal detecting unit) for detecting a myopotential signal (biosignal) that is generated when the joint at the shoulder, elbow, etc., is moved; and a torque sensor for detecting a driving force transmitted from a motor to the joint.

The body member 2 and the upper arm member 3 are mutually rotatably coupled by a shoulder joint mechanism 5. The upper arm member 3 and the forearm member 4 are mutually rotatably coupled by an elbow joint mechanism 6. The wearable motion assistive device 1 may have a structure similar to the above-described upper-right portion in an upper-left portion thereof.

The shoulder joint mechanism 5 and the elbow joint mechanism 6 aid the movements of the joint at the shoulder and the elbow, respectively. The wearable motion assistive device 1 also includes a control unit 100 having a control circuit for controlling drive units 11 for the shoulder joint mechanism 5 and the elbow joint mechanism 6. The control unit 100 controls each drive unit 11 based on the physical quantities and the biosignal detected by the angle sensor, the torque sensor, and the biosignal detecting sensor.

The control unit 100 controls the drive unit 11 using an autonomous control unit 100A and a voluntary control unit 100B in combination. The autonomous control unit 100A, when fed with a sensor signal (physical information signal) detected by each sensor, compares the detection value from each sensor with a reference parameter stored in a database to estimate a task and a phase of the wearer. The autonomous control unit 100A then generates an autonomous control signal for causing the drive units 11 to generate a driving force corresponding to the estimated phase. The voluntary control unit 100B generates a voluntary control signal based on a biopotential signal detected by a biopotential sensor 310. A control signal composing unit 100C generates a control signal for the drive units 11 by composing the voluntary control signal from the voluntary control unit 100B and the autonomous control signal from the autonomous control unit 100A.

In the following, the shoulder joint mechanism 5 is described in detail. Because the elbow joint mechanism 6 has substantially the same structure as the shoulder joint mechanism 5, corresponding parts or components with the same functions are designated by similar reference numerals while omitting the detailed description of the elbow joint mechanism 6.

Figure 2:
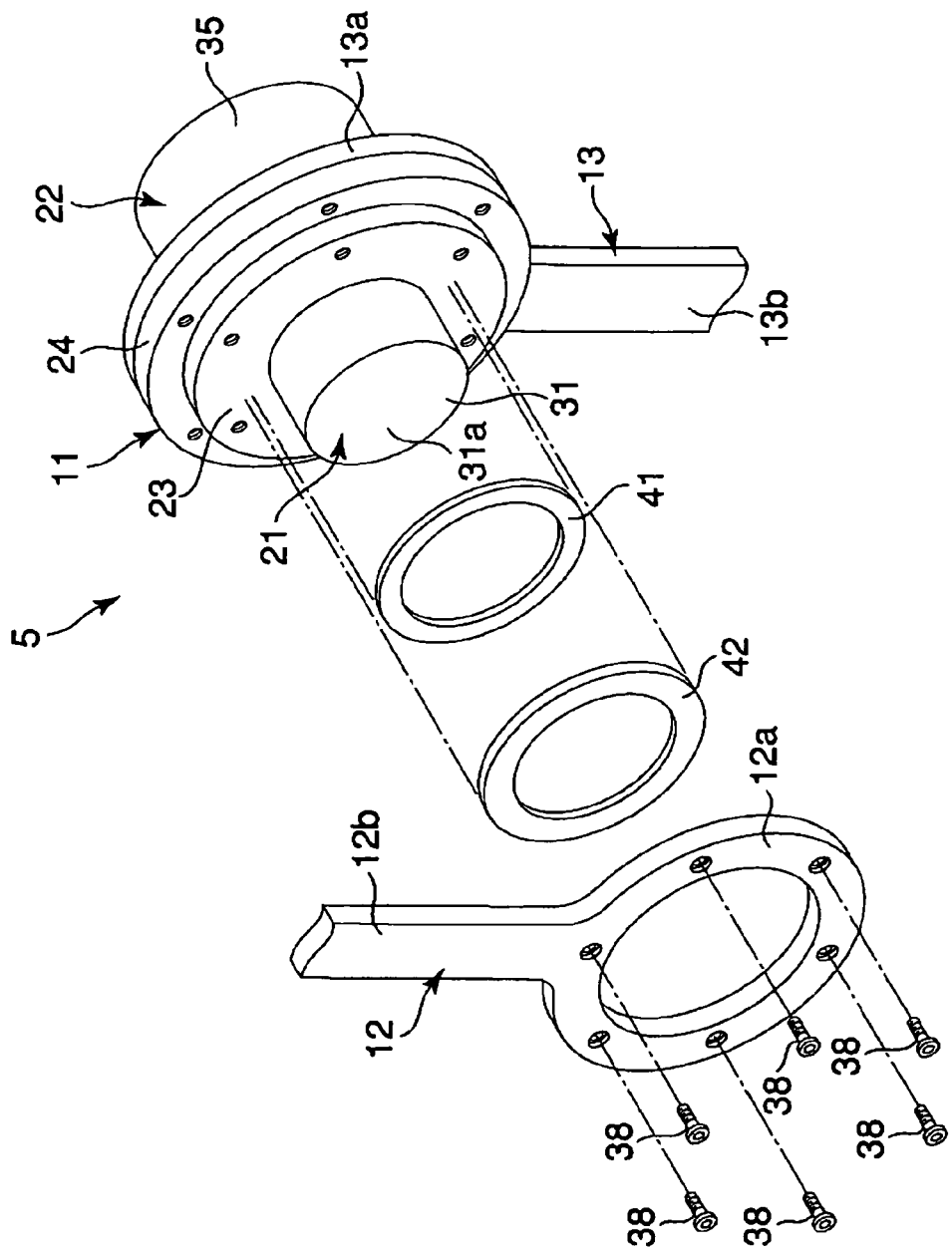
FIG. 2 shows a perspective view of a drive unit according to the first embodiment.
Figure 3:
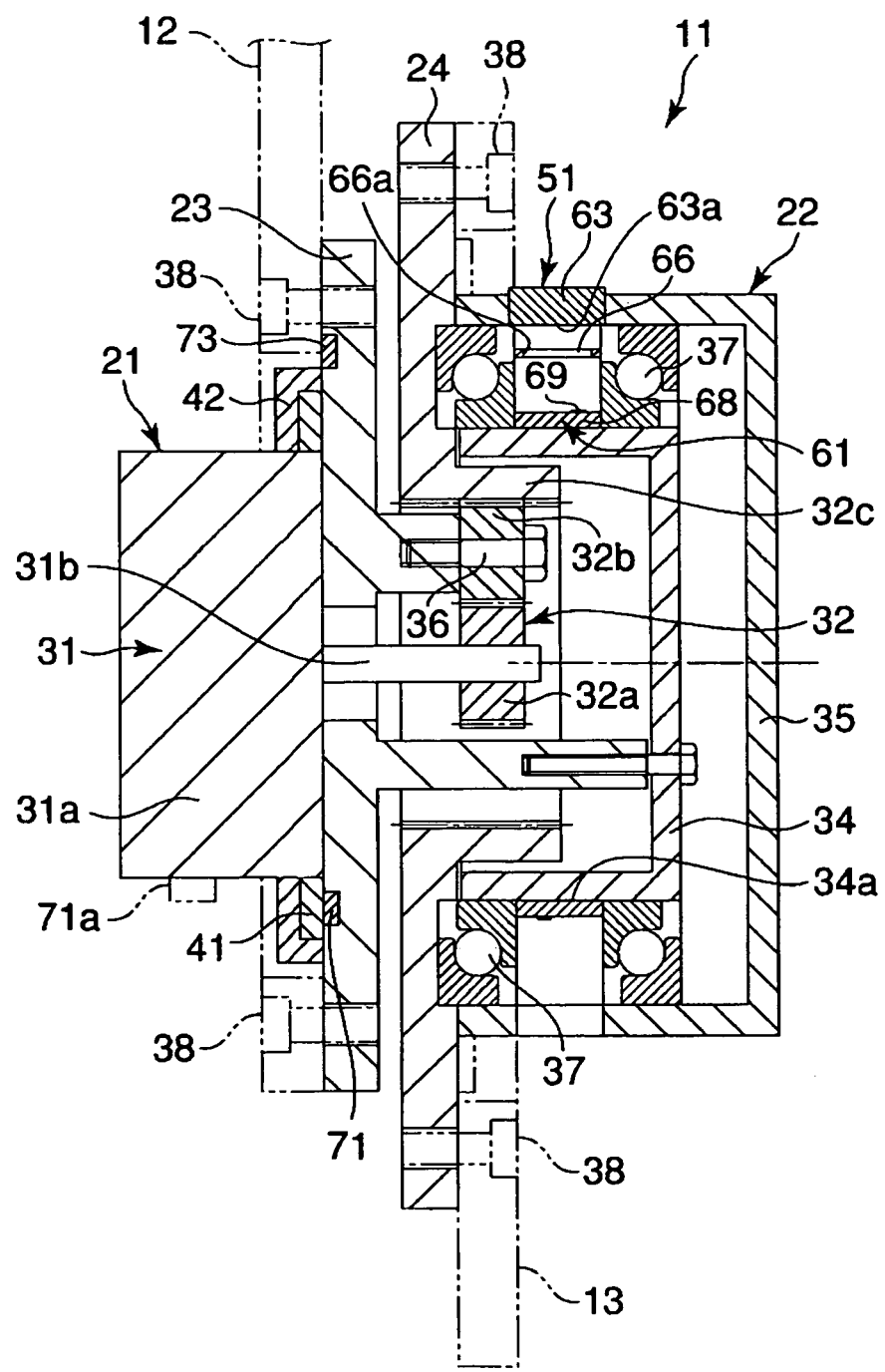
FIG. 3 shows a cross section of the drive unit according to the first embodiment.

With reference to FIGS. 2 and 3, the shoulder joint mechanism 5 includes first and second connecting members 12 and 13, as well as the drive unit 11. As shown in FIG. 1, one end of the first connecting member 12 is secured to the body member 2. One end of the second connecting member 13 is secured to the upper arm member 3.

As shown in FIG. 3, the drive unit 11 includes a drive portion 21, a gear head 22, and first and second flange members 23 and 24 that are rotatable relative to each other. The drive portion 21 has a motor 31 as a drive source. The motor 31 includes a motor body 31a and a drive shaft 31b. As shown in FIG. 3, the drive shaft 31b extends into the gear head 22. At the end of the drive shaft 31b, there is mounted a sun gear 32a that forms a part of a planetary gear mechanism 32.

The gear head 22 includes two housings: an inner case 34 and an outer case 35. The inner case 34 is an example of what the present invention refers to as a rotating body. The inner case 34 is also an example of a first component. The inner case 34 is formed in the cylindrical shape having one open end. The inner case 34 houses the planetary gear mechanism 32 inside. The planetary gear mechanism 32, in addition to the aforementioned sun gear 32a, may include plural planetary gears 32b in meshed engagement with the sun gear 32a, and an internal gear 32c (or so-called "ring gear") in meshed engagement with the planetary gears 32b. The planetary gear mechanism 32 is just an example of a reduction mechanism; the gear head 22 may adopt other types of reduction mechanisms. The inner case 23 may house a single gear rather than the plural gears.

Referring to FIG. 3, the first flange member 23 is fixed to the motor body 31a so that the first flange member 23 is in thermal connection with the motor 31. The planetary gear mechanism 32 includes a support member 36, such as bolts, for supporting the planetary gears 32b. The support member 36 may be fixed to the first flange member 23, to which the inner case 34 is fixed. Thus, the inner case 34 is stationary relative to the motor 31.

The outer case 35 is formed in the cylindrical shape having one open end. The outer case 35 houses the inner case 34. Between the outer case 35 and the inner case 34, there may be disposed plural bearing members 37. The second flange member 24 may be formed integrally with the internal gear 32c of the planetary gear mechanism 32. The outer case 35 is fixed to the second flange member 24 so that they can rotate together.

Referring to FIG. 2, the first connecting member 12 includes a ring-shaped fixing portion 12a and an extension 12b that extends from the fixing portion 12a. The end of the extension 12b is attached to the body member 2. The fixing portion 12a may be fixed to the first flange member 23 via plural bolts 38. The second connecting member 13 includes a ring-shaped fixing portion 13a and an extension 13b extending from the fixing portion 13a. The end of the extension 13b is attached to the upper arm member 3. The fixing portion 13a may be fixed to the second flange member 24 via plural bolts 38.

Hereafter, an operation of the drive unit 11 is described.

When the motor 31 is driven, the internal gear 32c rotates via the sun gear 32a and the planetary gears 32b. Thus, the second flange member 24 rotates relative to the first flange member 23. As the second flange member 24 rotates relative to the first flange member 23, an inner circumferential surface 35a of the outer case 35 rotates relative to an outer circumferential surface 34a of the inner case 34. The "rotation of B relative to A" herein is intended to refer to B rotating with respect to A; it also includes a rotation of A relative to a stationary B.

As the first flange member 23 rotates relative to the second flange member 24, the upper arm member 3 rotates relative to the body member 2. Thus, the motion of the wearer P moving his or her upper arm around the shoulder is assisted. Similarly, the drive unit 11 of the elbow joint mechanism 6 is configured to rotate the forearm member 4 relative to the upper arm member 3, thereby assisting the motion of the wearer P moving the forearm around the elbow.

In the present embodiment, the relative rotation of the inner case 34 to the outer case 35 is achieved by rotating the outer case 35 about the stationary inner case 34. In another embodiment, the first connecting member 12 may be fixed to the upper arm member 3 and the second connecting member 13 may be fixed to the body member 2. In this case, the inner case 34 rotates within the stationary outer case 35.

Figure 8:
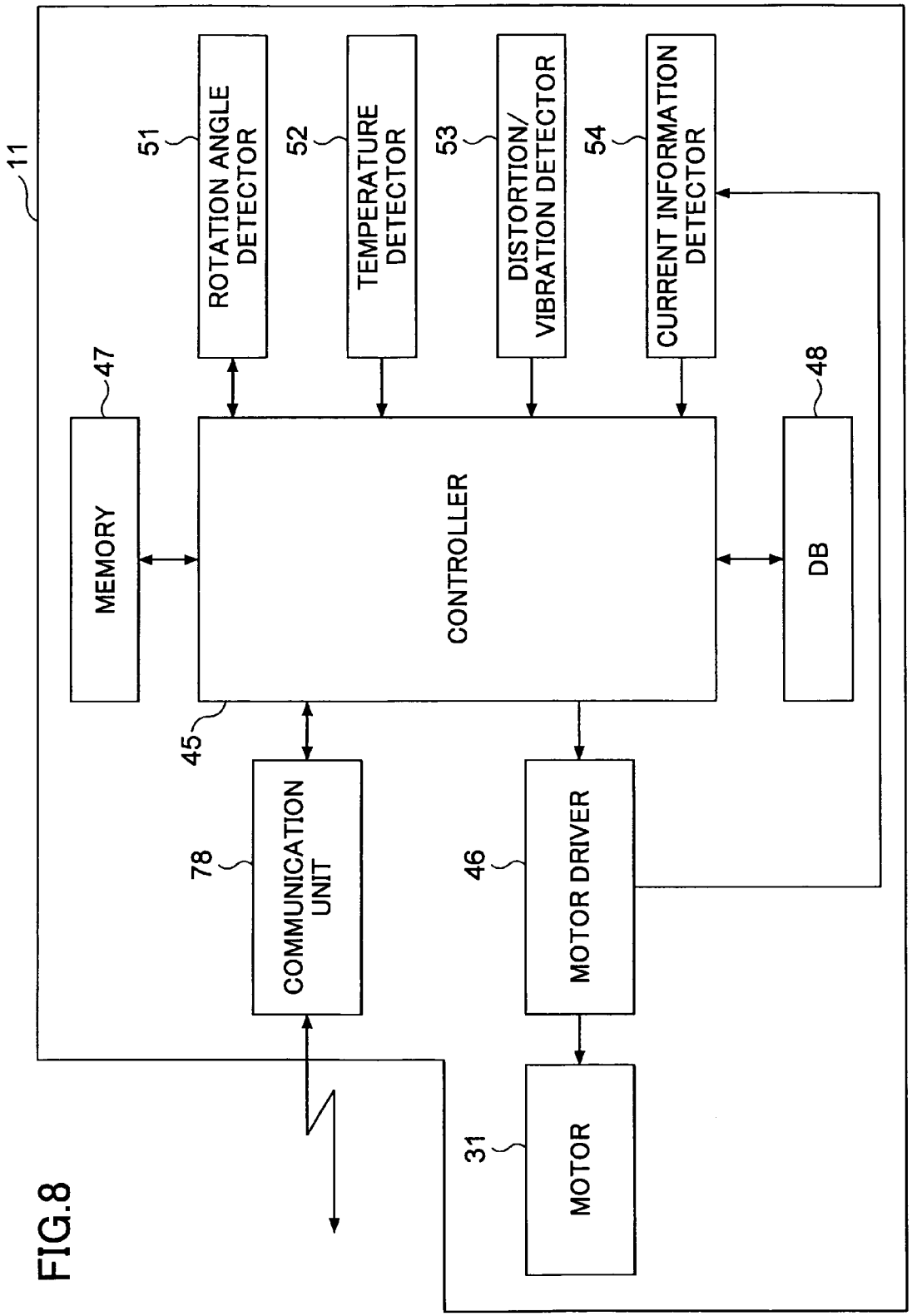
FIG. 8 shows a diagram of the drive unit according to the first embodiment.

As shown in FIG. 2, the drive unit 11 includes a circuit board 41 for controlling the motor 31. The circuit board 41 is formed in the shape of a ring larger than the outer shape of the motor body 31a. The circuit board 41 is mounted on the first flange member 23 in thermal connection therewith. The circuit board 41 utilizes the first flange member 23 as a heatsink. On the first flange member, a packing 42 is provided to cover the circuit board 41 so that the circuit board 41 is not exposed to the outside. As shown in FIG. 8, the circuit board 41 includes a controller 45 that generally controls the drive unit 11, a motor driver 46 for controlling the motor 31, a memory unit 47, and a database 48.

The drive unit 11 may include a rotation angle detecting unit 51, a temperature detecting unit 52, a distortion/vibration detecting unit 53, and a current information detecting unit 54.

Figure 9:
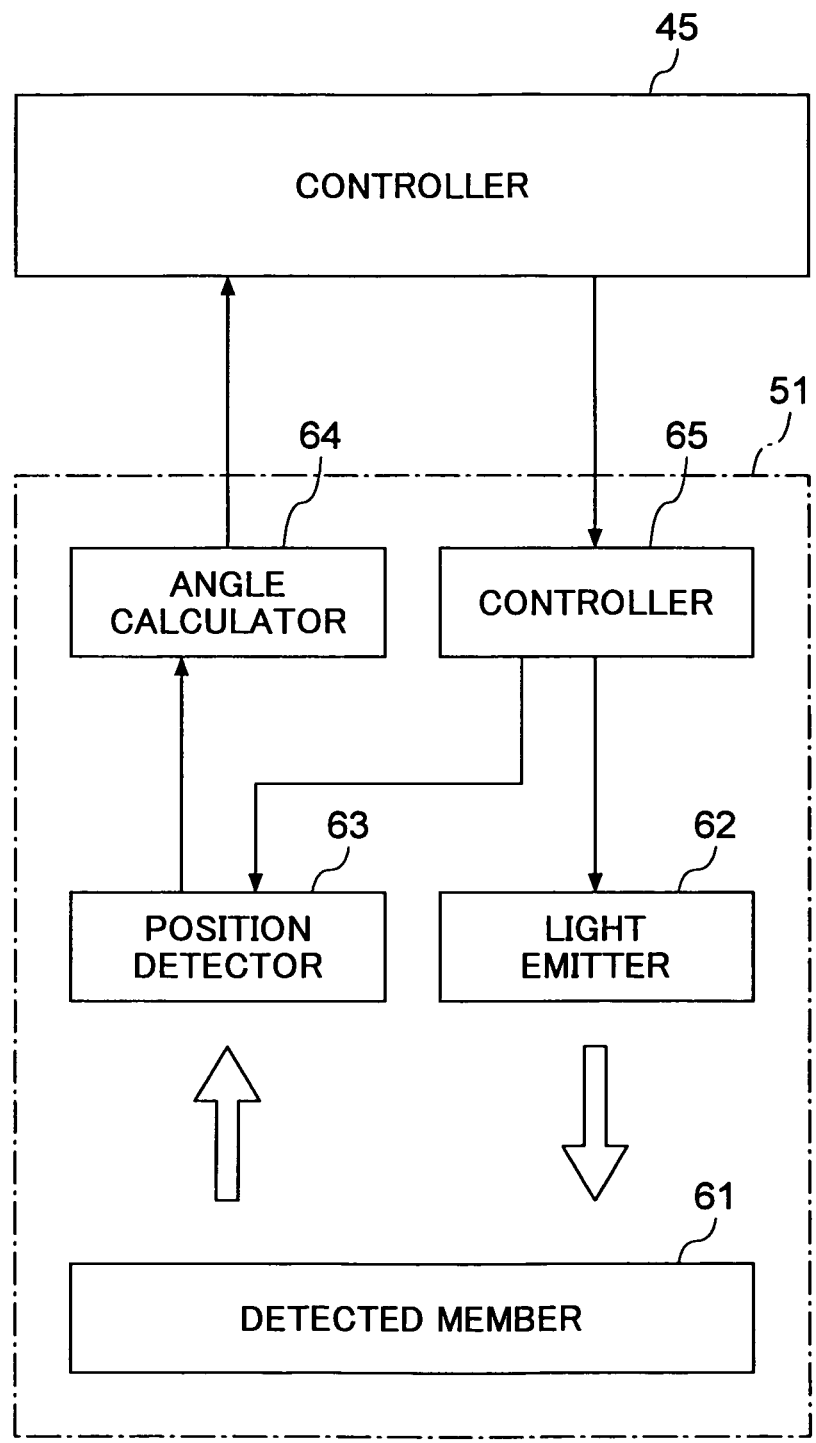
FIG. 9 shows a diagram of a rotation angle detecting unit according to the first embodiment.

As shown in FIGS. 3 and 9, the rotation angle detecting unit 51 includes a detected member 61, a light-emitting portion 62, a position detecting unit 63, an angle calculating unit 64, a controller 65, and a slit member 66.

Figure 4:
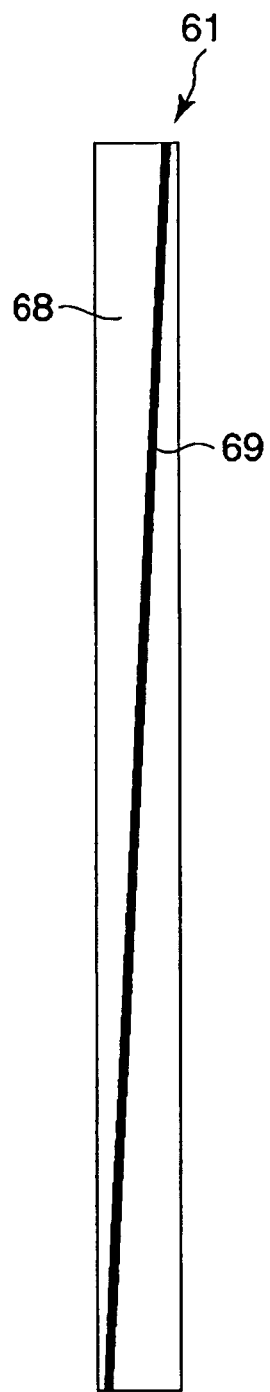
FIG. 4 shows a plan view of a detected member according to the first embodiment.

As shown in FIG. 4, the detected member 61 includes a main body 68 and a fluorescent band 69 provided on the main body 68. One example of the main body 68 is a thin band of flexible material. The main body 68 may be made of any material, such as resin, rubber, paper, etc., as long as its fluorescence is small.

Figure 5:
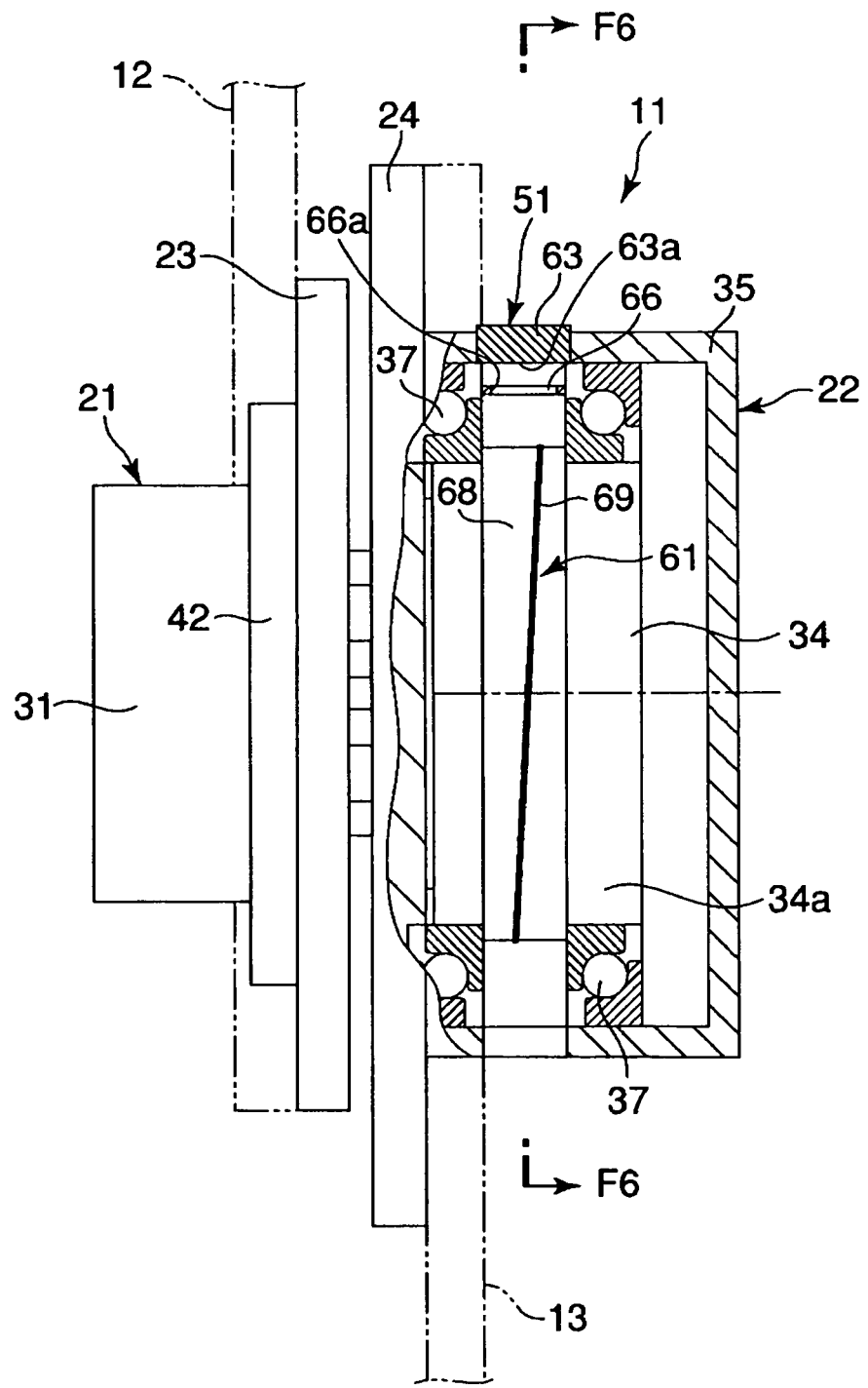
FIG. 5 shows a partially cross-sectional side view of the drive unit according to the first embodiment.
Figure 6:
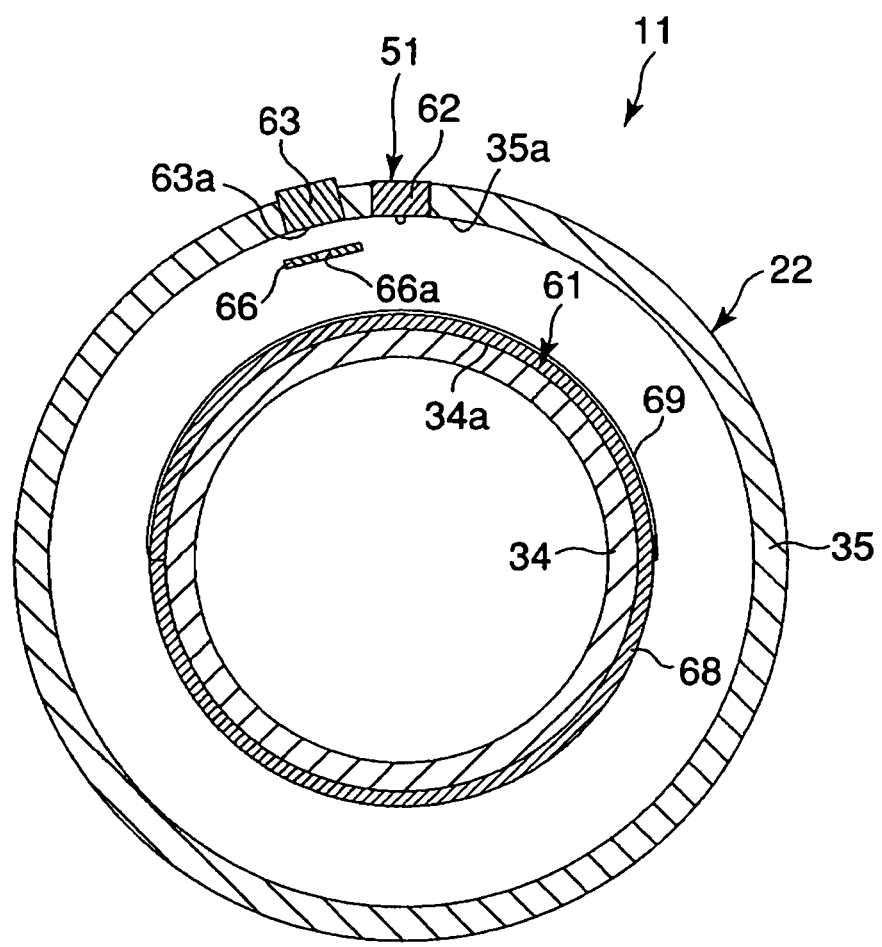
FIG. 6 shows a cross section of the drive unit taken along line F6-F6 of FIG. 5.

With reference to FIGS. 5 and 6, the main body 68 is wound around the outer circumferential surface 34a of the inner case 34 along a circumferential direction thereof. The main body 68 according to the present embodiment is formed in the shape of a closed loop that is wound around the outer circumferential surface 34a of the inner case 34 once. The main body 68 may be formed in the ring shape in advance. The main body 68 may be formed in the arc shape adapted to a necessary range of rotation angles to be detected, rather than the closed-loop shape.

As shown in FIG. 4, the fluorescent band 69 extends while inclined relative to the longitudinal direction of the main body 68. As shown in FIG. 5, when the main body 68 is wound around the inner case 34, the fluorescent band 69 extends spirally, i.e., inclined with respect to the circumferential direction of the inner case 34. Thus, when a specific point on the outer circumferential surface 34a of the inner case 34 is observed from the outside as the inner case 34 rotates relatively, the position of the fluorescent band 69 shifts along the axis of the inner case 34 (i.e., laterally in FIG. 5).

The "circumferential direction of the inner case 34" is herein intended to refer to a direction in which the inner case 34 rotates as it executes its relative rotation. Namely, it is a direction along the circumference of the cylindrical inner case 34 in accordance with the present embodiment. The fluorescent band 69 extends along the rotating direction of the inner case 34 so that the position of the fluorescent band 69 shifts in a direction perpendicular to the rotation direction of the inner case 34.

The fluorescent band 69 may comprise a fluorescent tape affixed to the main body 68; or it may be drawn on the main body 68 using fluorescent paint. Alternatively, the fluorescent band 69 may be directly provided on the outer circumferential surface 34a of the inner case 34. The "fluorescence" herein is intended to refer to the light emitted by substances in general that emit light upon irradiation with light, thus including the phosphorescence, in which light emission persists after the exciting source is removed. The fluorescent band 69 may have a width in a range from 10 μm to 20 μm. The width of the fluorescent band 69 is not limited to such range, however.

The light-emitting portion 62 may be fixed to the outer case 35 as shown in FIG. 6. The light-emitting portion 62 irradiates the detected member 61 with light. The light-emitting portion 62 may comprise a point light source including a light-emitting diode (LED).

The controller 65 controls the timing of light irradiation by the light-emitting portion 62. The controller 65 may send a pulsed control signal to the light-emitting portion 62 so that the light-emitting portion 62 can repeatedly turn on and off alternately, thereby irradiating the detected member 61 intermittently. In a non-limiting example, the light-emitting portion 62 is turned on and off at the cycle of 1 kHz.

The position detecting unit 63 may include a one-dimensional position detector element. One example of the one-dimensional position detector element is a position sensitive detector (PSD). The position detecting unit 63 may be attached to the outer case 35 as shown in FIGS. 5 and 6. Namely, the position detecting unit 63 is stationary relative to the outer case 35. The position detecting unit 63 has a light-receiving surface 63a that is disposed opposite the detected member 61.

The position detecting unit 63 is disposed with a one-dimensional detection line thereof lying along the axis of the inner case 34. When a spot of light is incident on the position detecting unit 63, the position detecting unit 63 can detect the position of entry of the spot light along the axis of the inner case 34. Thus, the position detecting unit 63 can detect the location of the fluorescent band 69 (position information about the fluorescent band 69 in the axial direction of the inner case 34) within an area opposite the light-receiving surface 63a.

The controller 65 sends a control signal to the position detecting unit 63 that is synchronized with the control signal sent to the light-emitting portion 62. The controller 65 controls the position detecting unit 63 so that the position detecting unit 63 performs the position detection process for the fluorescent band 69 when the light-emitting portion 62 is turned off (i.e., when the light-emitting portion 62 is not emitting light).

The position information about the fluorescent band 69 detected by the position detecting unit 63 is sent to the angle calculating unit 64. The angle calculating unit 64 performs a process for calculating a relative rotation angle between the outer case 35 and the inner case 34 from the position information about the fluorescent band 69. The calculation may be based on information regarding the inclined angle of the fluorescent band 69, or the position information about the fluorescent band 69 at a reference position (at the rotation angle 0°. The angle calculating unit 64 sends the information about the calculated rotation angle to the controller 45.

The slit member 66 is disposed between the position detecting unit 63 and the inner case 34. The slit member 66 may be fixed to the outer case 35 so that they can move together. The slit member 66 has a slit 66a opposite the light-receiving surface 63a of the position detecting unit 63. The slit 66a extends along the axis of the inner case 34.

Hereafter, an operation of the rotation angle detecting unit 51 is described.

When the control signal regarding the irradiation timing is sent from the controller 65 to the light-emitting portion 62, the light-emitting portion 62 irradiates the detected member 61 with light intermittently in accordance with the irradiation timing. The controller 65 causes the position detecting unit 63 to stand by when the light-emitting portion 62 is on and perform detection when the light-emitting portion 62 is off.

When the light-emitting portion 62 is on, the detected member 61 is irradiated with light so that the fluorescent band 69 is charged with light energy. When the light-emitting portion 62 is off, the fluorescent band 69 emits light. Light emitted by the fluorescent band 69 located along the detection line of the position detecting unit 63 passes through the slit 66a and becomes incident on the position detecting unit 63. Light emitted by the fluorescent band 69 that is located outside the detection line is blocked by the slit member 66 and therefore does not become incident on the position detecting unit 63.

The position detecting unit 63 detects position information concerning the fluorescent band 69 opposite the position detecting unit 63 based on the incident position of light. The angle calculating unit calculates a rotation angle based on the position information about the fluorescent band detected by the position detecting unit 63, and then sends the calculated information to the controller 45.

Hereafter, the temperature detecting unit 52 is described.

Figure 10:
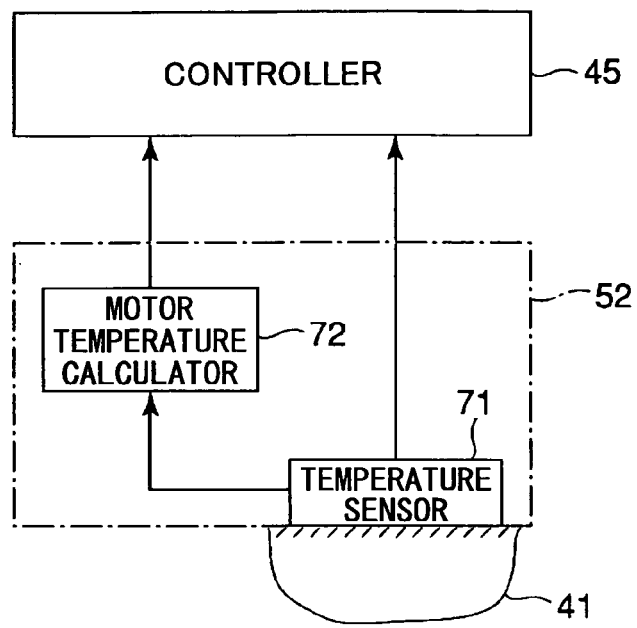
FIG. 10 shows a temperature detecting unit according to the first embodiment.

With reference to FIG. 10, the temperature detecting unit 52 includes a temperature sensor 71 for detecting a temperature of the circuit board 41 on which the controller 45 is mounted, and a motor temperature calculating unit 72. The temperature sensor 71 is in contact with the circuit board 41, as shown in FIG. 3. Thus the temperature sensor 71 can directly detect the temperature of the circuit board 41. The temperature sensor 71 sends information about the detected temperature to the controller 45 and also to the motor temperature calculating unit 72.

The motor temperature calculating unit 72, based on the detected temperature received from the temperature sensor 71, calculates a temperature of the motor 31 by solving a one-dimensional heat equation. The motor temperature calculating unit 72 sends information about the calculated temperature of the motor 31 to the controller 45. The detection of the temperature of the circuit board 41 and that of the motor 31 are performed continuously during the operation of the drive unit 11. In another embodiment, the temperature detecting unit 52 may comprise a separate temperature sensor 71a for directly detecting the temperature of the motor 31, as indicated by two-dot chain lines in FIG. 3, instead of the motor temperature calculating unit 72.

Hereafter, the distortion/vibration detecting unit 53 is described.

Figure 11:
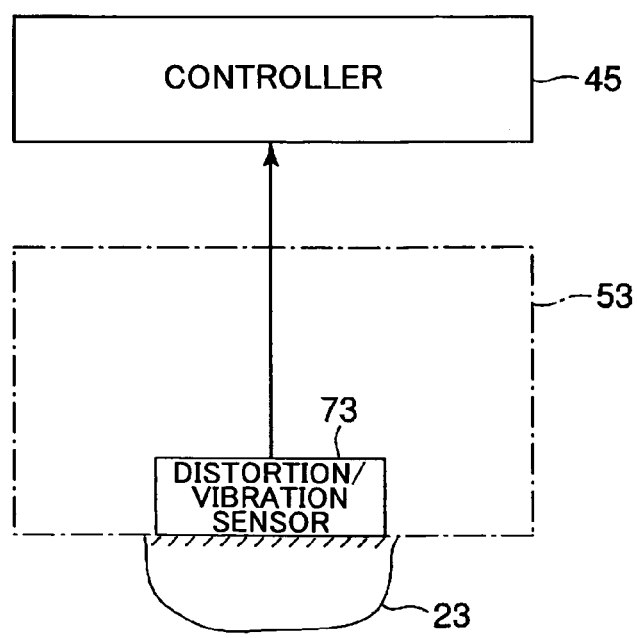
FIG. 11 shows a diagram of a distortion/vibration detecting unit according to the first embodiment.

With reference to FIG. 11, the distortion/vibration detecting unit 53 includes a distortion/vibration sensor 73. The distortion/vibration sensor 73 is attached to the first flange member 23, as shown in FIG. 3. The distortion/vibration sensor 73 detects an amount of distortion in the first flange member 23 and also a state of vibration (such as the presence or absence of chattering vibration) of the first flange member 23. The detection of the distortion amount and the vibration state is performed continuously during the operation of the drive unit 11.

Hereafter, the current information detecting unit 54 is described.

Figure 12A:
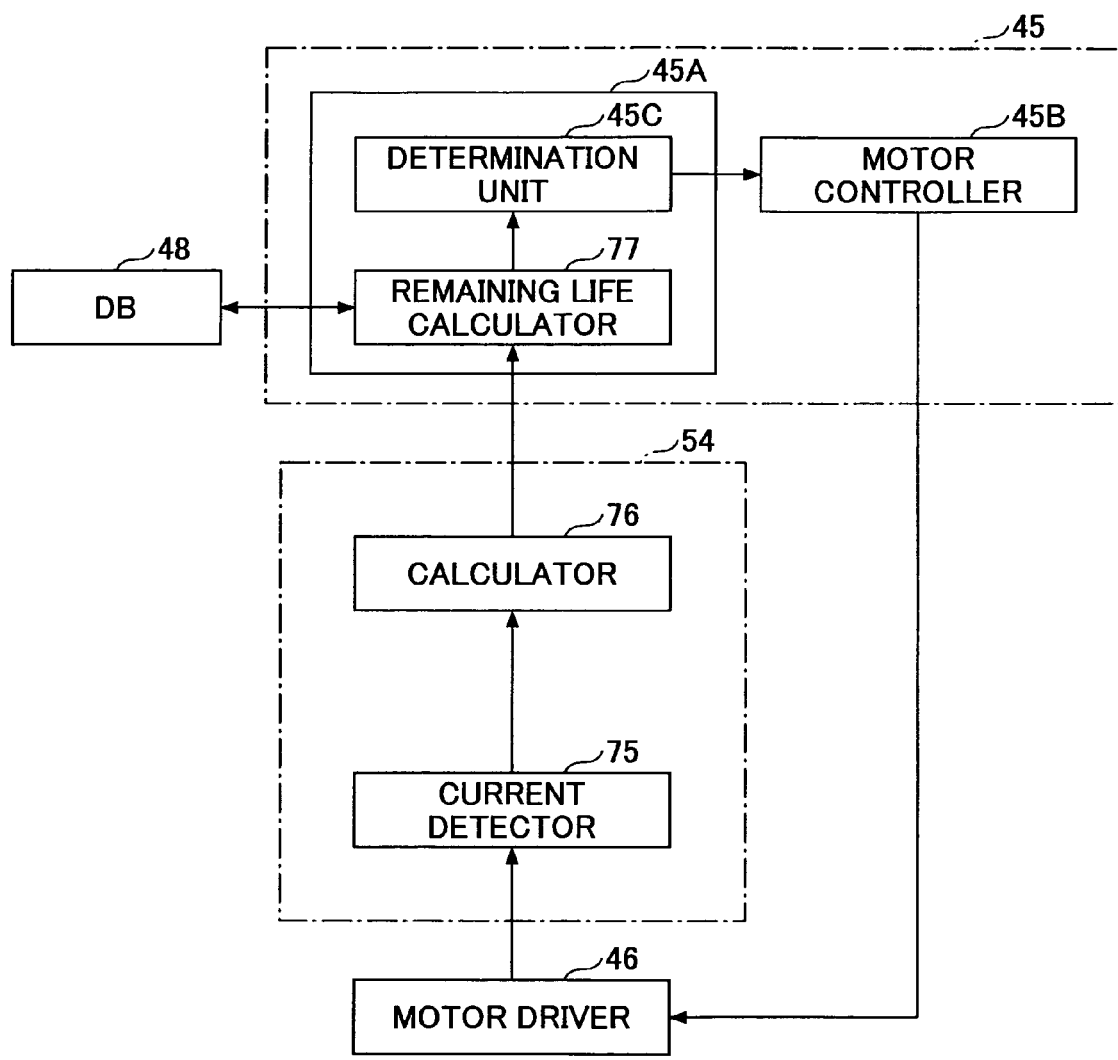
FIG. 12A shows a diagram of a current information detecting unit according to the first embodiment.

With reference to FIG. 12A, the current information detecting unit 54 includes a current detecting unit 75 and a calculating unit 76. The current detecting unit 75 may detect a value of electric current that flows in the motor 31 by measuring an electric current flowing in the motor driver 46. The current detecting unit 75 sends information about the detected current value to the calculating unit 76. The calculating unit 76 integrates the value of electric current flow in the motor 31 since the initial startup of the drive unit 11 with respect to time, to calculate how much current has flowed through the motor 31 since the initial startup time of the drive unit 11 up to the present time. The calculating unit 76 sends a time-integrated current value (total operation time) to the controller 45.

In the database 48, there is stored data concerning an allowable temperature of the circuit board 41 for preventing malfunction; an allowable temperature of the motor 31 for preventing malfunction; an allowable distortion amount of the first flange member 23; and the life of the motor 31, for example.

The controller 45 includes a motor monitoring unit 45A for monitoring an operational status of the motor 31, and a motor controller 45B for limiting a drive signal to the motor 31 based on a result of monitoring by the motor monitoring unit 45A in order to prevent an overload state of the motor 31. Further, the motor monitoring unit 45A includes a determination unit 45C for determining whether the total integrated value of the current supplied to the motor 31 exceeds a preset threshold, and a remaining life calculating unit 77. When the determination unit 45C determines that the total integrated value of current exceeds the preset threshold, the motor controller 45B controls the motor 31 so that the drive signal supplied to the motor 31 is gradually decreased at a predetermined rate (such as decreasing at the rate of 5% to 10% of the maximum output per second).

The controller 45 compares information about the temperatures of the circuit board 41 and the motor 31 received from the temperature detecting unit 52 with the acceptable values stored in the database 48 and the total operation time of the motor 31 with an average life of the motor 31. When it is likely that either the temperature of the circuit board 41 or that of the motor 31 will exceed the acceptable values, the controller 45 reduces or terminates the driving of the motor 31 by, e.g., switching to a slower speed. The controller 45 compares the distortion amount or the state of vibration sent from the distortion/vibration detecting unit 53 with the acceptable values stored in the database, and reduces or terminates the driving of the motor 31 as needed.

Thus, the drive unit 11 can prevent the forcible driving of the motor 31 when the performance of the motor 31 is lowered, or the overheating of the motor 31. Thus, when it is likely that the motor 31 and the circuit board 41 will be put in an overload state if a normal drive signal is fed to the motor 31 when the performance of the motor 31 is dropped due to aging or the like, the drive signal is gradually decreased so that the driving force of the motor 31 can be reduced, thereby extending the life of the motor 31. Such extension of life of the motor 31 particularly contributes to the lessening of burden on the wearer when the drive unit 11 is embedded within the wearer's body (see FIGS. 23 and 24) where the motor 31 cannot be easily replaced.

When the remaining lifetime of the motor 31 has reached a preset value, the drive signal supplied to the motor 31 is gradually decreased at the predetermined rate (such as at the rate of 5% to 10% of the maximum output per second). Thus sudden performance drop in the motor 31 in response to the drive signal can be prevented. This enables the prevention of sudden deactivation of the motor 31 and the resultant total loss of driving force in the motor 31 against the will of the wearer.

As shown in FIG. 12A, the controller 45 includes the remaining life calculating unit 77. The remaining life calculating unit 77 receives from the current information detecting unit 54 information about the time-integrated value of the electric current that has flowed through the motor 31. In the database 48, there is stored information about the time-integrated current values associated with the end of life of the motor as determined by experiment or actual use (such as a preset reference value for determining a lifetime). The remaining life calculating unit 77 compares the time-integrated current value received from the current information detecting unit 54 with the information stored in the database, in order to calculate a remaining life of the motor 31. For example, the controller 45 determines that it is the replacement time when the time-integrated value of the electric current flow through the motor 31 exceeds a predetermined reference value. The detection of remaining life is performed continuously during the operation of the drive unit 11.

As shown in FIG. 8, the drive unit 11 includes a communication unit 78. The memory unit 47 receives various information about the values detected or calculated by the temperature detecting unit 52, the distortion/vibration detecting unit 53, the current information detecting unit 54, and the controller 45. The memory unit 47 also stores history information about the above information. The communication unit 78 may comprise a radio communication unit. The communication unit 78 may transmit the various information detected or calculated by the temperature detecting unit 52, the distortion/vibration detecting unit 53, the current detecting unit 75, and the controller 45 to the outside periodically.

FIG. 12B shows a graph plotting the drive current in the motor 31 versus time. As shown in FIG. 12B, the drive current in the motor 31 changes over time depending on the angle and torque when the shoulder or elbow joint is driven. In accordance with the present embodiment, a first acceptable value $I_A$ and a second acceptable value $I_B$ of the drive current are set in the database 48 in advance ($I_A<I_B$).

The drive unit 11 includes the database (storage unit) 48, in which the first acceptable value $I_A$ and the second acceptable value $I_B$ higher than the first acceptable value $I_A$ of the current value supplied to the motor 31 are stored. The remaining life calculating unit 77 calculates a remaining life by integrating an excess current value above the first acceptable value $I_A$ and subtracting the total use time up to the present time from an average life. When the calculated integrated value exceeds a threshold, the motor controller 45B controls the motor 31 so that the electric current supplied to the motor 31 gradually decreases at a predetermined rate (such as at the rate of 5% to 10% of the first acceptable value $I_A$ per second).

Also, the motor controller 45B, when the drive current exceeds the second acceptable value $I_B$, controls the motor 31 so that the electric current supplied to the motor 31 gradually decreases at a predetermined rate. The rate at which the current value is decreased may be set as follows. For example, the current value in excess of the second acceptable value $I_B$ is reduced to the second acceptable value $I_B$ instantaneously (such as within one second), or to the first acceptable value within several seconds. Alternatively, the drive current may be reduced smoothly by using a sigmoid function, a Bézier curve, or a spline curve.

When the exceeding of the drive current beyond the second acceptable value $I_B$ is detected repeatedly, the control unit 100 automatically sets an assist ratio (the ratio of torque produced by the drive unit to torque produced by the wearer) lower. The aforementioned predetermined rate may be set to any desired value depending on the particular situation. For example, the drive current is reduced at the rate in a range from 0.1% to 1% of the maximum output per second before the motor 31 is stopped.

Hereafter, a main control process for the motor 31 performed by the controller 45 of the drive unit 11 is described with reference to FIG. 13A.

In response to a drive instruction from the control unit 100 to the drive unit 11, the controller 45 starts to drive the motor 31 in a first step S1. Following the first step S11, in a second step S12, the current information detecting unit 54 detects a value of electric current that flows in the motor 31 and calculates a time-integrated value of the current value (monitoring unit). In a third step S13, the temperature detecting unit 52 detects a temperature of the circuit board 41 and calculates a temperature of the motor 31 (monitoring unit). In a fourth step S14, the distortion/vibration detecting unit 53 detects an amount of distortion and a vibration state in the first flange member 23 (monitoring unit). In accordance with the present embodiment, the second to the fourth steps S2, S3, and S4 are performed simultaneously. Alternatively, these steps may be performed sequentially in any order.

In a fifth step S5, the controller 45 compares the various information detected in the second through the fourth steps S2, S3, and S4 with the acceptable values or reference values stored in the database 48, and determines whether the operating status of the drive unit 11 is normal (determination unit). For example, the controller 45 determines whether the time-integrated value of the current flow through the motor 31 is below the predetermined amount; whether the temperature of the circuit board 41 is below the acceptable value; whether the temperature of the motor 31 is below the acceptable value; whether the distortion amount of the first flange member 23 is below the acceptable value; and whether there is any sign of chattering vibration based on the vibration state.

When all of those values are below the respective acceptable values, the rotation angle detecting unit 51 in a sixth step S6 detects a relative rotation angle of the first and the second flange members 23 and 24. In a seventh step S7, the controller 45 determines whether a stop position is reached based on the detected rotation angle. When the controller 45 determines that the stop position is not yet reached, the process is repeated from the second step S2 sequentially. When the controller 45 determines that the stop position is reached, the motor 31 is stopped in an eighth step S8, thereby completing the process.

When any of the time-integrated value of the current flow through the motor 31, the temperature of the circuit board 41, the temperature of the motor 31, and the distortion amount of the first flange member 23 exceeds the acceptable value or the reference value, or when a sign of chattering vibration is observed in the fifth step S5, the routine of the process branches to a ninth step S9. In the ninth step S9, the driving of the motor 31 is reduced by, e.g., entering into a low-speed operation (motor control unit). Thus, when any of the acceptable values is exceeded in S5, a deceleration control is performed whereby the driving of the motor 31 is switched to a low-speed rotation at a predetermined rate, for example, in S9, thereby reducing the driving of the motor 31.

In a tenth step S10, information detected by the various detecting units is transmitted to the outside by the communication unit 78. The driving of the motor 31 is stopped at about the same time as the step S10.

Hereafter, a maintenance control process for the motor 31 performed by the controller 45 of the drive unit 11 is described with reference to FIG. 13B. The maintenance control process is performed in parallel with the above-described main control process (FIG. 13A), as an interrupt process at preset time intervals (such as at one-minute or 10-minutes intervals).

Figure 13A:
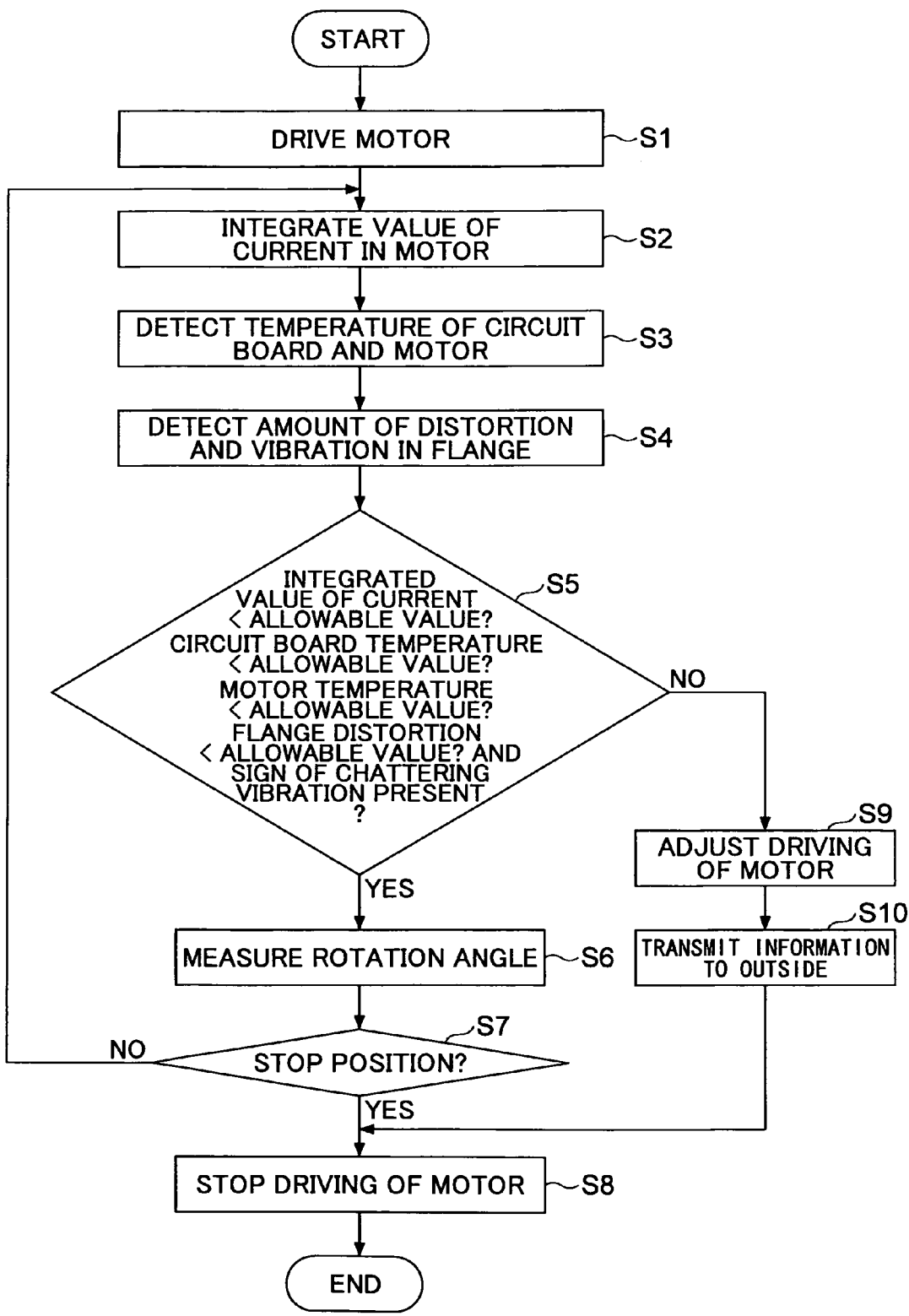
FIG. 13A shows a flowchart of a main control process performed by a controller 45 for the drive unit according to the first embodiment.
Figure 13B:
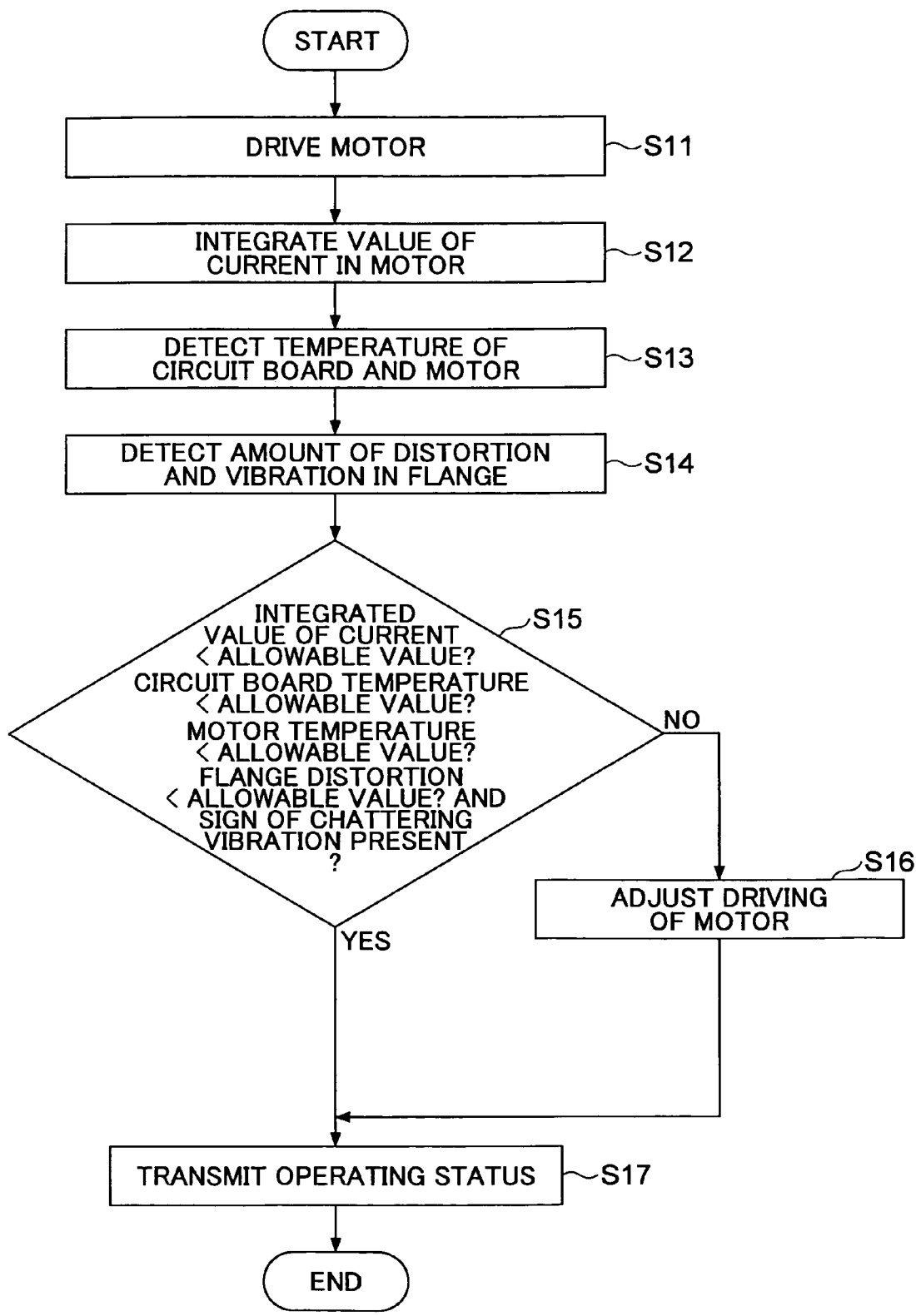
FIG. 13B shows a flowchart of a maintenance process for the drive unit according to the first embodiment performed by the controller 45.

With reference to FIG. 13B, the first through sixth steps S11 to S16 are the same as the first through fifth steps S1 to S5 and the ninth step S9 of FIG. 13A described above and are therefore not described.

The process shown in FIG. 13B differs from the process of FIG. 13A in the seventh step S17. In step S17, the controller 45 transmits the operating status of the motor (such as whether the time-integrated value of current flow through the motor 31 is below the predetermined amount; whether the temperature of the circuit board 41 is below the acceptable value; whether the temperature of the motor 31 is below the acceptable value; whether the distortion amount of the first flange member 23 is below the acceptable value; and whether there is a sign of chattering vibration based on the vibration state) to an information management apparatus 84 at a center (see FIG. 7) via the communication network 83. Thus, the operating status of the individual wearable motion assistive device 1 can be analyzed in the information management apparatus 84 based on a database 88 at the center.

Finally, a maintenance management system 81 of the wearable motion assistive device 1 is described.

Figure 7:
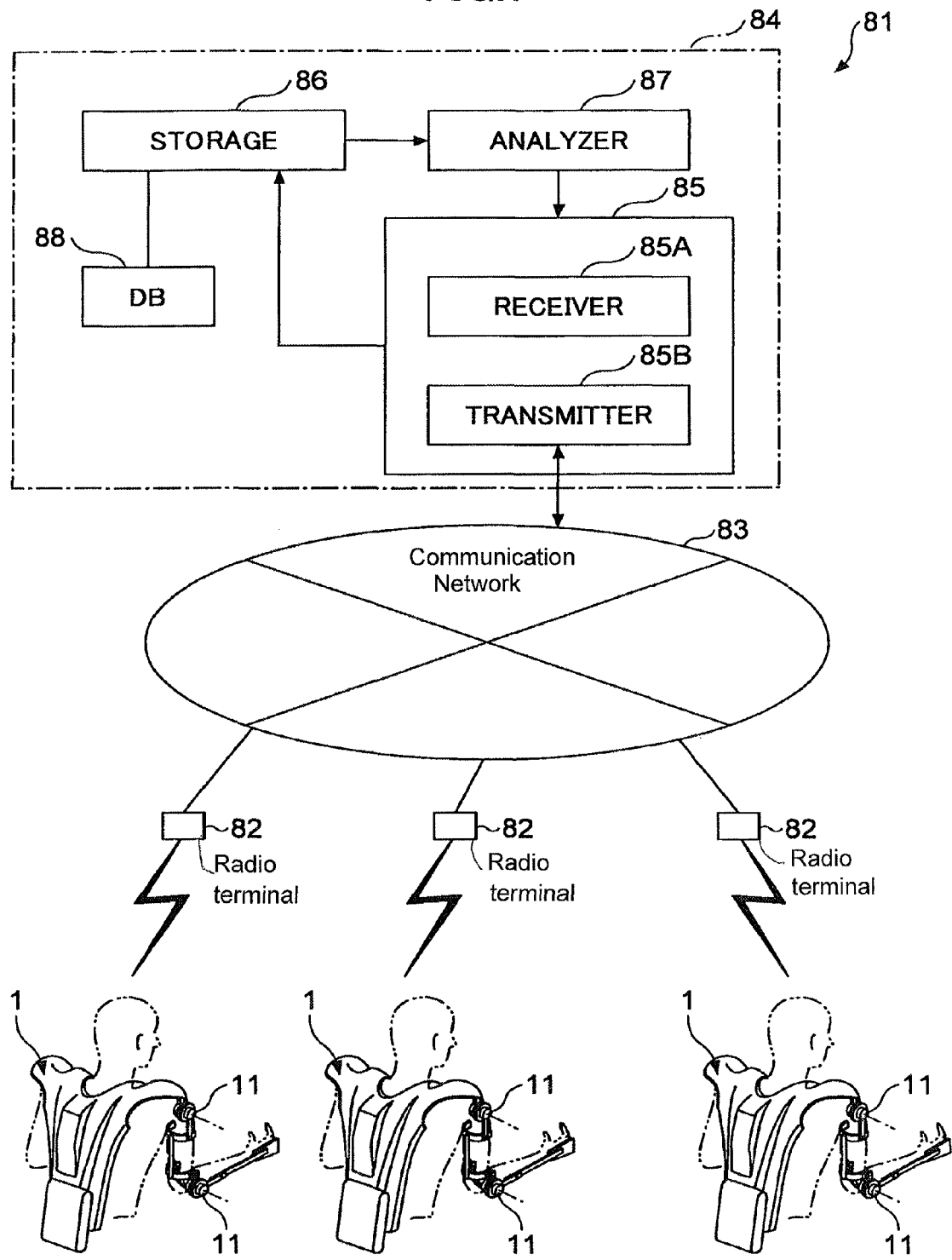
FIG. 7 shows a diagram of a maintenance management system including the wearable motion assistive device according to the first embodiment.

As shown in FIG. 7, the maintenance management system 81 includes the wearable motion assistive device 1 and the radio terminal 82 provided on the part of each user, and the information management apparatus 84 provided on the part of the supplier and connected to the user-side radio terminal 82 via the communication network 83, such as the Internet.

The information management apparatus 84 at the center is configured to manage the operational status of the wearable motion assistive device 1. The information management apparatus 84 includes a communication unit 85 connected to the communication network 83; a storage unit 86 including the database 88 for successively storing information (including the history information about the motor 31) about the operational status of the individual wearable motion assistive device 1 that is inputted via the communication unit 85; and an analyzing unit 87 for analyzing the wearable motion assistive device 1 based on the information about the individual operational status stored in the storage unit 86.

The analyzing unit 87 analyzes the history information stored in the database 88 to generate analysis information which may concern the life of the drive unit 11 or the presence or absence of an overload state in the drive unit 11. When serious analyzed result is obtained, the analyzing unit 87 transmits the related analysis information to the relevant wearable motion assistive device 1.

The communication unit 85 includes a receiver unit 85A and a transmitter unit 85B. The receiver unit 85A receives history information about the drive status of the motor 31 that is transmitted from the drive unit 11 via the communication unit 78 and the communication network 83. The transmitter unit 85B, when it is determined that maintenance of the motor 3 is required based on the analysis result obtained by the analyzing unit, transmits maintenance information to the relevant drive unit 11.

The wearable motion assistive device 1 thus includes the communication unit 78 for the individual drive unit 11 as described above. Specifically, the wearable motion assistive device 1 includes plural communication units 78, such as the communication unit 78 provided for the drive unit 11 of the shoulder joint mechanism 5, and the communication unit 78 provided for the drive unit 11 for the elbow joint mechanism 6. These plural communication units 78 send information about the operating status of each drive unit 11 onto the communication network 83 periodically, for example, via the radio terminals 82. Similarly, another wearable motion assistive device 1 being used by another user also sends information about the individual drive units 11 onto the communication network 83. The information management apparatus 84 provided on the supplier end receives the information from each user via the communication network 83, and centrally manages the information on the database 88.

Thus, the history information about the drive status of the motor 31 transmitted from the drive unit 11 via the communication unit and the communication network 83 is stored in the database 88 at the center for managing the operational status of the motion assistive device. The history information stored in the database 88 is analyzed to obtain an analysis result based on the information about the life of the drive unit 11 or the presence or absence of an overload state. Based on such analysis result, maintenance information is transmitted to the relevant drive unit 11. In this way, whether the drive unit 11 is normal can be constantly analyzed, so that the wearer can be immediately notified via a radio alert signal in the event of some form of abnormality in the drive unit 11.

In accordance with the wearable motion assistive device 1 or the drive unit 11 having the above-described structures, the influence of the scattering of light in the rotation angle detecting unit 51 can be curbed, so that an improved rotation angle detection accuracy can be achieved. Namely, in the rotation angle detecting unit 51 according to the present embodiment, because the fluorescent band 69 emits light by itself, there is no problem of the scattering of light at the edge of the fluorescent band 69, whereby the light without scattering becomes incident on the position detecting unit 63. Thus, the use of the fluorescent band 69 prevents an error due to the scattering of light, thereby improving the rotation angle detection accuracy.

The light-emitting portion 62 emits light intermittently and the position detecting unit 63 receives the light emitted by the fluorescent band 69 when the light-emitting portion 62 is turned off. Thus, the light emitted by the fluorescent band 69 can be reliably detected without interference from the light emitted by the light-emitting portion 62.

The detected member 61 comprises the main body 68 with the fluorescent band 69 attached thereon. This structure enables more accurate setting of the inclination angle of the fluorescent band 69 relative to the circumferential direction than when the fluorescent band 69 is directly attached to a rotating body. The mounting of the fluorescent band 69 is also simplified.

Generally, in many angle detecting units, a rotating shaft coupled to a motor shaft is fitted with an angle detecting portion. Consequently, the size of a drive unit having such an angle detecting unit becomes large in the axial direction. On the other hand, in the detected member 61 according to the present embodiment, the detected member 61 is attached to the outer circumferential surface 34a of the inner case 34, which is a gear case. This eliminates the need for an angle detecting portion on the rotating axle, thereby reducing the size of the drive unit 11.

When an angle detector such as a potentiometer is used, a detection error may be caused by a misalignment or distortion between the potentiometer shaft and the rotating shaft. On the other hand, in accordance with the present embodiment, because the rotation angle detecting unit 51 is directly built inside the gear/motor system, detection error does not easily occur and a highly reliable detection can be realized.

The slit member 66 is not necessarily required and may be omitted. The slit member 66, when provided, blocks excess light from the front or rear of the detection line, thereby improving the rotation angle detection accuracy.

For example, in the monitoring system according to Patent Document 3, the operating status of the motor is monitored by a sensor, and an alert is issued if data concerning the operating status exceeds a threshold. When a drive unit is equipped with such a monitoring system, a supplier of the drive unit needs to respond to individual drive units every time an alert is issued.

In an aspect of the present invention, a drive unit is provided in which an operating status of the motor 31 is monitored, and an active corrective operation is performed to achieve an appropriate operating status.

Because the first flange member 23 is thermally connected with the motor 31, the temperature of the first flange member 23 increases when the motor 31 is driven. If a circuit board, which also generates heat, is mounted on such flange member, the temperature of the circuit board may become excessively high. For this reason, circuit boards are generally located away from motors.

In accordance with the present embodiment, in the drive unit 11, the circuit board 41 is mounted on the first flange member 23. The drive unit 11 includes the temperature detecting unit 52 for detecting the temperature of the circuit board 41. The temperature of the circuit board 41 is constantly monitored by the temperature detecting unit 52. When it is likely that the temperature will exceed an acceptable value, the amount of heat transferred from the motor 31 to the first flange member 23 is reduced by, for example, reducing the driving of the motor 31. In this way, the first flange member 23 can function properly as a heatsink for the circuit board 41, thereby controlling the temperature increase in the circuit board 41. By thus monitoring the temperature status of the circuit board 41 and controlling the motor 31 by the controller 45, the circuit board 41 can be mounted on the first flange member 23, which is thermally connected to the motor 31. Because the circuit board 41 can be located adjacent the motor 31, the size of the drive unit 11 can be reduced.

For example, as the temperature detecting unit 52 monitors the temperature of the motor 31 and when the temperature of either the motor 31 or the circuit board 41 is likely to exceed the acceptable value, the driving of the motor 31 is reduced. As a result, with the first flange member 23 functioning as a heatsink for the motor 31 or the circuit board 41, excess temperature increase can be prevented. Thus, the size of the drive unit 11 can be reduced and improved reliability can be obtained.

The motor 31 used in the wearable motion assistive device 1 is not so much rotated a great number of times during its life as it is typically used in an overload state for supporting a heavy load, for example. As a method of detecting the remaining life of the motor 31, the total number of revolutions of the motor could be counted. However, this is not suitable for the motor 31 for the wearable motion assistive device 1.

In the drive unit 11 according to the present embodiment, the controller 45 determines the life of the motor 31 by time-integrating the value of electric current that flows in the motor 31 from the time of initial operation. The overload state of the motor 31 is largely dependent on the magnitude of the electric current that flows through the motor 31. Thus, by calculating the time-integrated value of the electric current, the degree of overloading of the motor 31 can be roughly determined. In this way, the drive unit 11 can appropriately determine the life of the motor 31 in an overload state.

The memory unit 47 in the drive unit 11 stores various detected information or the like, providing information about the kind of environment that the drive unit 11 has been used in up to the present time. Such information enables improvement in maintenance efficiency, for example.

The communication unit 78 in the drive unit 11 transmits the various detected information to the outside, enabling the monitoring of the operating status and the determination of the remaining life of the individual drive unit 11 externally. Thus, it becomes possible for the supplier end to indicate a suggested replacement time, or to prepare replacement parts for the drive unit 11 that is about to reach its replacement time.

When each of the plural drive units 11 is constructed as an independent unit having the various detecting units 52, 53, and 54, the circuit board 41 including the controller 45, and the communication unit 78, the individual drive units 11 need to be only connected via power supply cables, thus making the wearable motion assistive device 1 more convenient to use.

In the present embodiment, the fluorescent band 69 is installed on the inner case 34 and the position detecting unit 63 is mounted on the outer case 35. In another embodiment, the fluorescent band 69 may be installed on the outer case 35 and the position detecting unit 63 may be mounted on the inner case 34.

The position detecting unit 63 may not be configured to detect light when the light-emitting portion 62 is turned off. For example, the frequency of the light emitted by the fluorescent band 69 may be made different from that of the light emitted by the light-emitting portion 62, and the position detecting unit 63 may be configured to respond to the frequency of the fluorescent band 69. In this way, the position detecting unit 63 can perform the position detection process based on the light emitted by the fluorescent band 69 even when the light-emitting portion 62 is turned on. However, the selection or adjustment of the position detecting unit 63 is easier and detection error is less likely to develop by performing the detection process when the light-emitting portion 62 is turned off.

Figure 15:
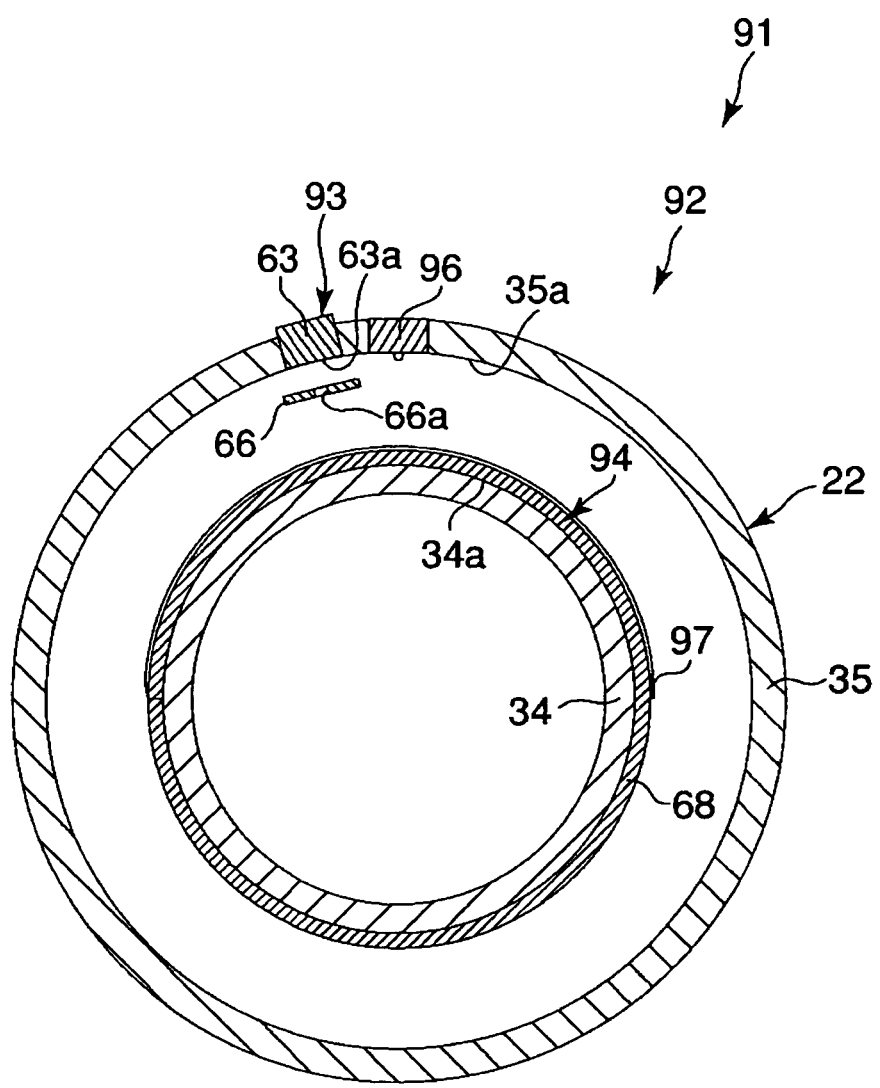
FIG. 15 shows a cross section of the drive unit taken along line F15-F15 of FIG. 14.
Figure 16:
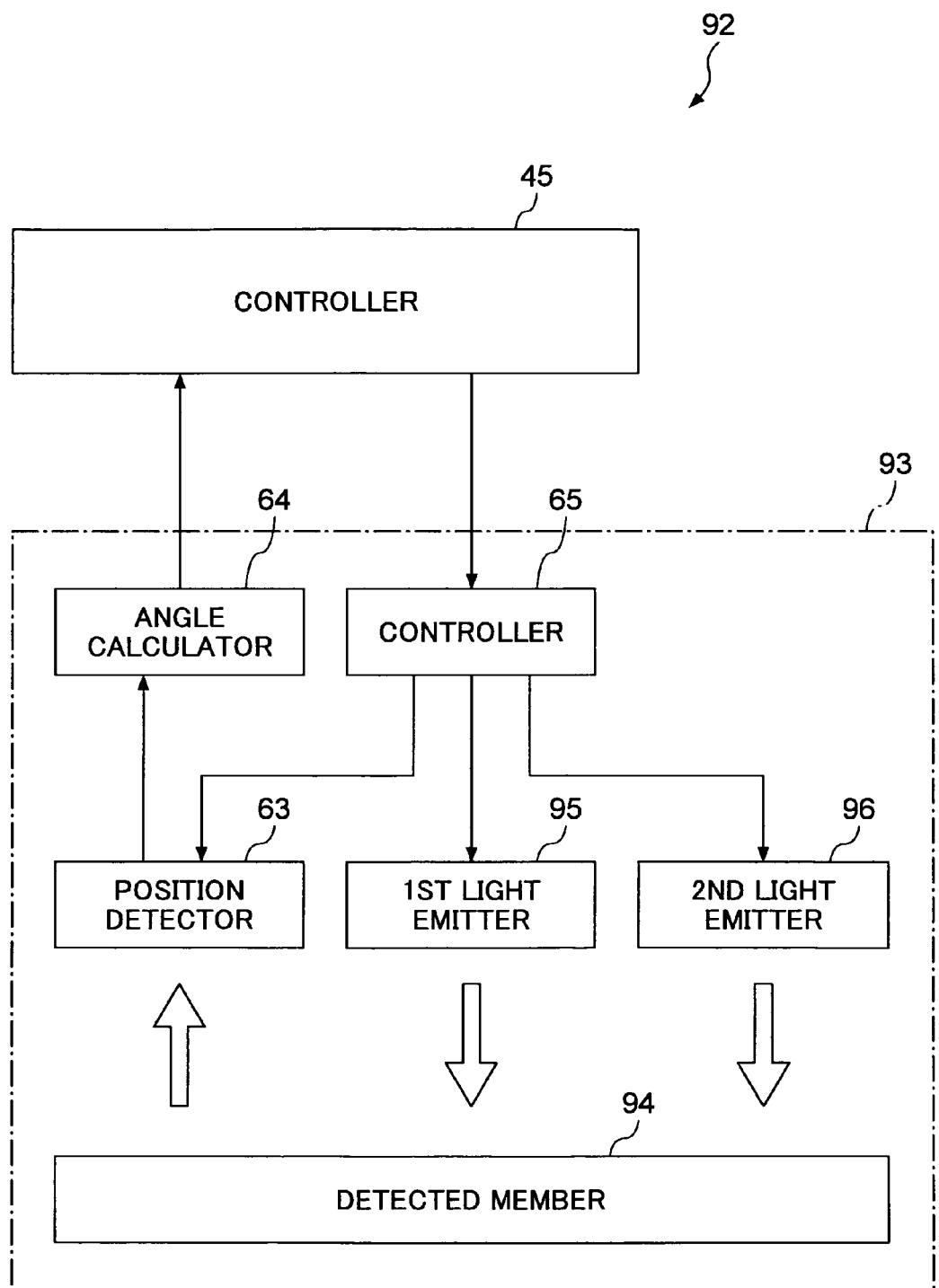
FIG. 16 shows a rotation angle detecting unit according to the second embodiment.

Hereafter, a wearable motion assistive device 91 according to a second embodiment of the present invention is described with reference to FIGS. 14 to 16. Parts or elements having the same functions as those of the wearable motion assistive device 1 of the first embodiment are designated with similar reference numerals and their description is omitted.

The wearable motion assistive device 91 includes a shoulder joint mechanism 5 and an elbow joint mechanism 6, each having a drive unit 92. The drive unit 92 is similar to the drive unit of the first embodiment, with the exception of a rotation angle detecting unit 93 which differs from the rotation angle detecting unit 51 of the first embodiment. Specifically, the drive unit 92 includes a controller 45, a motor driver 46, a memory unit 47, a database 48, a temperature detecting unit 52, a distortion/vibration detecting unit 53, and a current information detecting unit 54.

The rotation angle detecting unit 93 includes a detected member 94, a first light-emitting portion 95, a second light-emitting portion 96, a position detecting unit 63, an angle calculating unit 64, a controller 65, and a slit member 66.

The detected member 94 includes a main body 68 and a reflecting band 97 installed on the main body 68. In an example, the main body 68 is painted black to reduce light reflectivity.

The reflecting band 97 extends while inclined in the longitudinal direction of the main body 68. As shown in FIG. 14, when the main body 68 is wound around the inner case 34, the reflecting band 97 extends spirally in the circumferential direction of the inner case 34. Thus, when the inner case 34 is relatively rotated, the position of the reflecting band 97 changes in the axial direction of the inner case 34. The reflecting band 97 is formed of a material with high light reflectivity. The reflecting band 97 may be provided by a light reflective tape affixed to the main body 68, or may be drawn with a light reflective paint. Alternatively, the reflecting band 97 may be directly provided on the outer circumferential surface of the inner case 34. In an example, the reflecting band 97 has a width in a range from 10 μm to 20 μm. The width of the reflecting band 97 however is not limited to such range.

Figure 14:
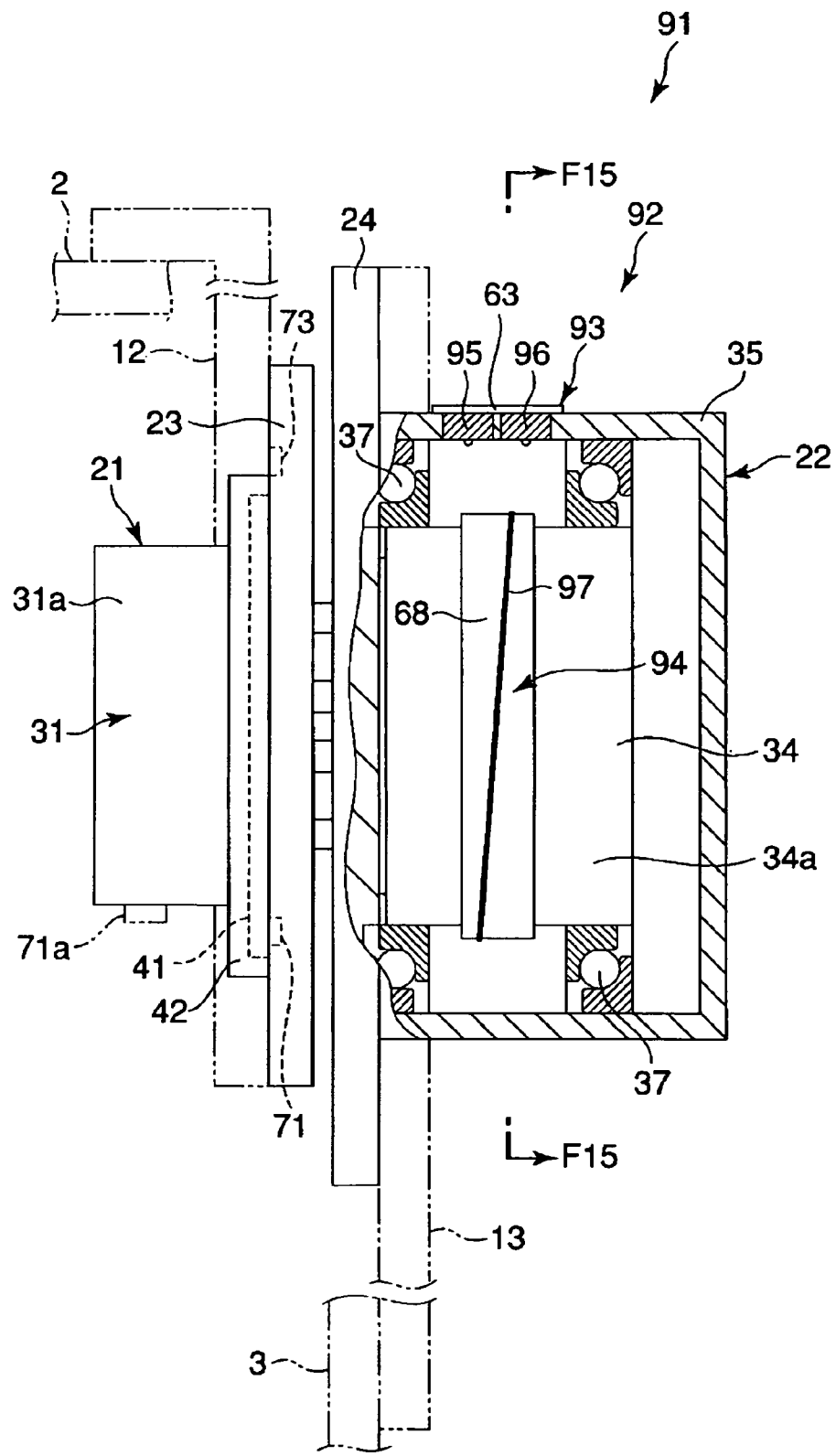
FIG. 14 shows a partially cross-sectional side view of a drive unit of a wearable motion assistive device according to a second embodiment of the present invention.

The first and the second light-emitting portions 95 and 96 may be fixed to the outer case 35, as shown in FIG. 14. The first and second light-emitting portions 95 and 96 are spaced apart from each other in the axis direction of the inner case 34. The first and second light-emitting portions 95 and 96 may be spaced apart from the center of the detected member 94 by the same distance in the opposite directions, along the axis of the inner case 34. The first and second light-emitting portions 95 and 96 are configured to irradiate the detected member 94 with light.

The controller 65 controls the timing of irradiation of the first and second light-emitting portions 95 and 96. The controller 65 may be configured to send a pulsed control signal to the first and second light-emitting portions 95 and 96 so that the first and second light-emitting portions 95 and 96 are turned on alternately. The first and second light-emitting portions 95 and 96 may be turned on and off at the period of 1 kHz; however, the first and second light-emitting portions may be turned on and off at other periods.

The position detecting unit 63 receives the light from the first light-emitting portion 95 that is reflected by the reflecting band 97 when the first light-emitting portion 95 is turned on. The position detecting unit 63 receives the light emitted by the second light-emitting portion 96 that is reflected by the reflecting band 97 when the second light-emitting portion 96 is turned on. Based on a distribution of the reflected light that is detected when the first light-emitting portion 95 is turned on, and a distribution of the reflected light detected when the second light-emitting portion 96 is turned on, the position detecting unit 63 detects position information about the reflecting band 97 in the axial direction of the inner case 34.

For example, the position detecting unit 63 detects the position of a peak ("first peak") of the distribution of the reflected light detected when the first light-emitting portion 95 is turned on, and the position of a peak ("second peak") of the distribution of the reflected light detected when the second light-emitting portion 96 is turned on. The position detecting unit 63 then determines an intermediate position between the first peak and the second peak as an instantaneous position of the reflecting band 97.

For example, the position detecting unit 63 detects the first and second peaks at a reference position (such as at the rotation angle 0° and a predetermined position (such as the rotation angle 180°. The position detecting unit 63 then determines the intermediate position at each position as reference position information and predetermined position information about the reflecting band 97, respectively. Such information is then stored in the angle calculating unit 64.

The angle calculating unit 64 receives the position information about the reflecting band 97 detected by the position detecting unit 63 at an arbitrary angle. Based on the reference position information and the predetermined position information and the like about the reflecting band 97, the angle calculating unit 64 calculates a relative rotation angle between the outer case 35 and the inner case 34.

The position information about the reflecting band 97 may be detected in other ways than by determining the intermediate position at the first and second peaks. Any method capable of identifying a position corresponding to a rotation angle from the reflected light distribution due to the first light-emitting portion 95 and the reflected light distribution due to the second light-emitting portion 96 can be suitably adopted.

In accordance with the wearable motion assistive device 91 or the drive unit 92 as described above, the influence of the scattering of light in the rotation angle detecting unit 93 can be curbed, so that improved rotation angle detection accuracy can be achieved. Specifically, the reflected light distribution due to the first light-emitting portion 95 and the reflected light distribution due to the second light-emitting portion 96 are different. This is because the diffuse reflection caused at the edge of the reflecting band 97 when the first light-emitting portion 95 is turned on differs from the diffuse reflection caused at the edge of the reflecting band 97 when the second light-emitting portion 96 is turned on, resulting in different scattering characteristics.

Thus, in the drive unit 11 according to the present embodiment, by detecting the position information about the reflecting band 97 based on the two reflected light distributions having different scattering characteristics, the probability of the detection result being influenced by the scattering in the individual light distribution can be reduced. In this way, the influence of the scattering of light at the edge of the reflecting band 97 can be curbed, whereby improved rotation angle detection accuracy can be achieved.

The edges of the reflecting band 97 on either side lie side by side along the axis of the inner case 34. By providing the first and second light-emitting portions 95 and 96 side by side along the axis of the inner case 34, the reflected light distribution due to the first light-emitting portion 95 and the reflected light distribution due to the second light-emitting portion 96 tend to differ from each other. As a result, the influence of the scattering of light at the edges can be further curbed, so that improved rotation angle detection accuracy can be obtained. When the first and second light-emitting portions 95 and 96 are spaced apart from the detected member 94 by the same distance in the opposite directions along the axis of the inner case 34, development of error becomes less likely so that improved detection accuracy can be achieved.

When the first and second light-emitting portions 95 and 96 emit light alternately, the mutually different two light distributions can be reliably obtained. Namely, by receiving the reflected light from the first light-emitting portion 95 with the position detecting unit 63 when the second light-emitting portion 96 is turned off, the reflected light from the first light-emitting portion 95 is not contaminated by the reflected light from the second light-emitting portion 96.

The first and second light-emitting portions 95 and 96 may not necessarily emit light alternately. For example, the first light-emitting portion 95 and the second light-emitting portion 96 may be configured to emit light with different frequencies. In this case, the position information about the reflecting band 97 can be detected from the two reflected light distributions caused by the first and second light-emitting portions 95 and 96 as they emit light simultaneously.

While in the present embodiment the inner case 34 is fitted with the reflecting band 97 and the outer case 35 is fitted with the position detecting unit 63, the outer case 35 may be fitted with the reflecting band 97 and the inner case 34 may be fitted with the position detecting unit 63.

Hereafter, a wearable motion assistive device 101 according to a third embodiment of the present invention is described with reference to FIGS. 17 and 18. Parts or elements with the same functions as those of the wearable motion assistive device 1 according to the first embodiment are designated with similar reference numerals and their description is omitted.

The wearable motion assistive device 101 includes a shoulder joint mechanism 5 and an elbow joint mechanism 6, each having a drive unit 102. The drive unit 102 is similar to the drive unit of the first embodiment with the exception of the rotation angle detecting unit 103 which differs from the rotation angle detecting unit 51 of the first embodiment.

The rotation angle detecting unit 103 includes a fluorescent band 69, a light-emitting portion 62, a position detecting unit 63, an angle calculating unit 64, a controller 65, and a slit member 66. In accordance with the present embodiment, the first flange member 23 is an example of what the present invention refers to as the first component; the second flange member 24 is an example of the second component.

Figure 18:
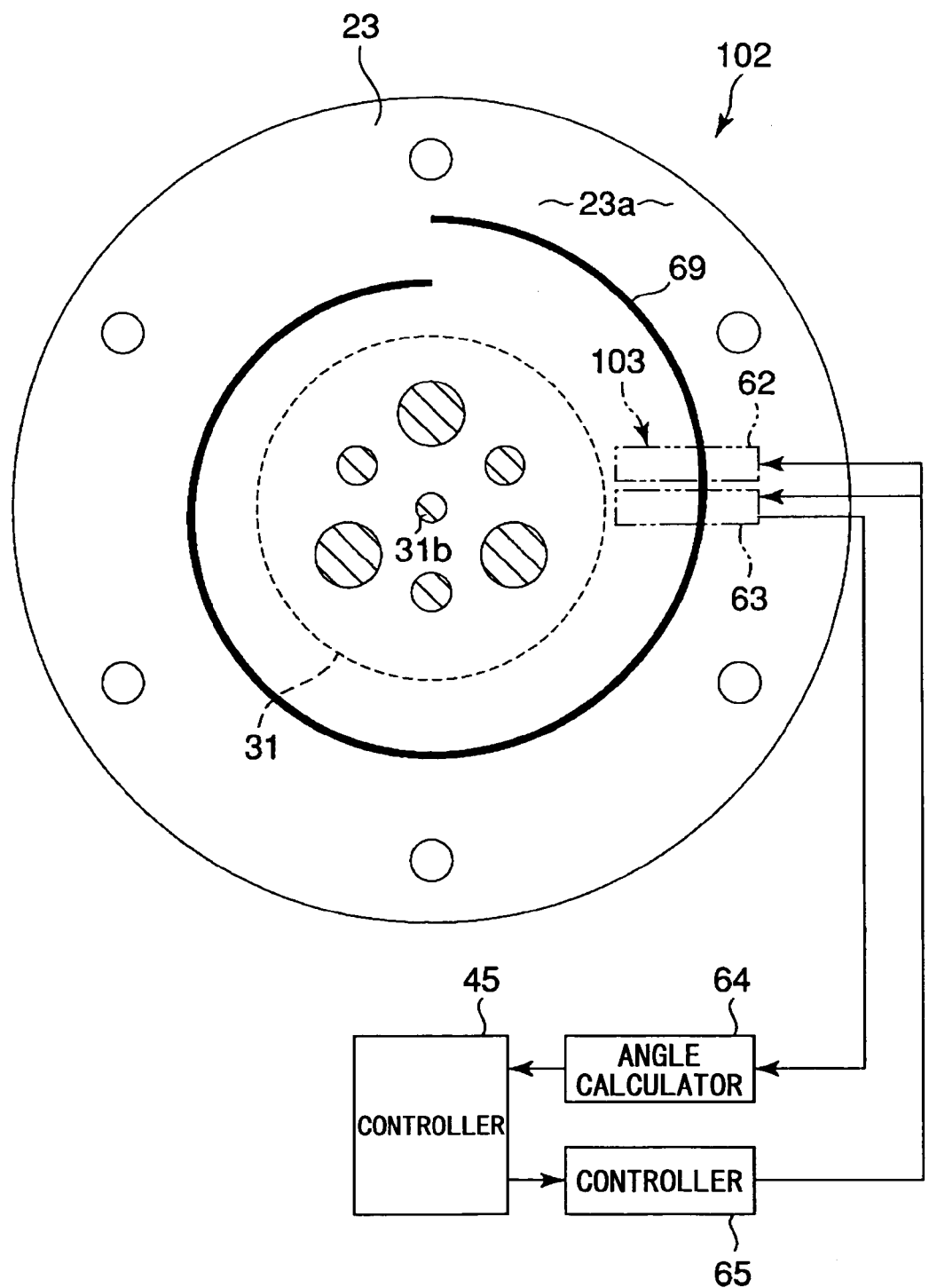
FIG. 18 shows a cross section of the drive unit taken along line F18-F18 of FIG. 17.

As shown in FIG. 18, the fluorescent band 69 is provided on an end face 23a of the first flange member 23. The fluorescent band 69 is disposed opposite the second flange member 24 and extends spirally. Namely, the fluorescent band 69 extends in the direction of rotation of the second flange member 24 such that the position of the fluorescent band 69 changes in a direction perpendicular to the direction of rotation of the second flange member 24 (which is the radial direction of the first flange member 23 in the present embodiment).

The light-emitting portion 62 may be fixed to the second flange member 24. The light-emitting portion 62 is turned on and off alternately so that the fluorescent band 69 is irradiated with light intermittently.

Figure 17:
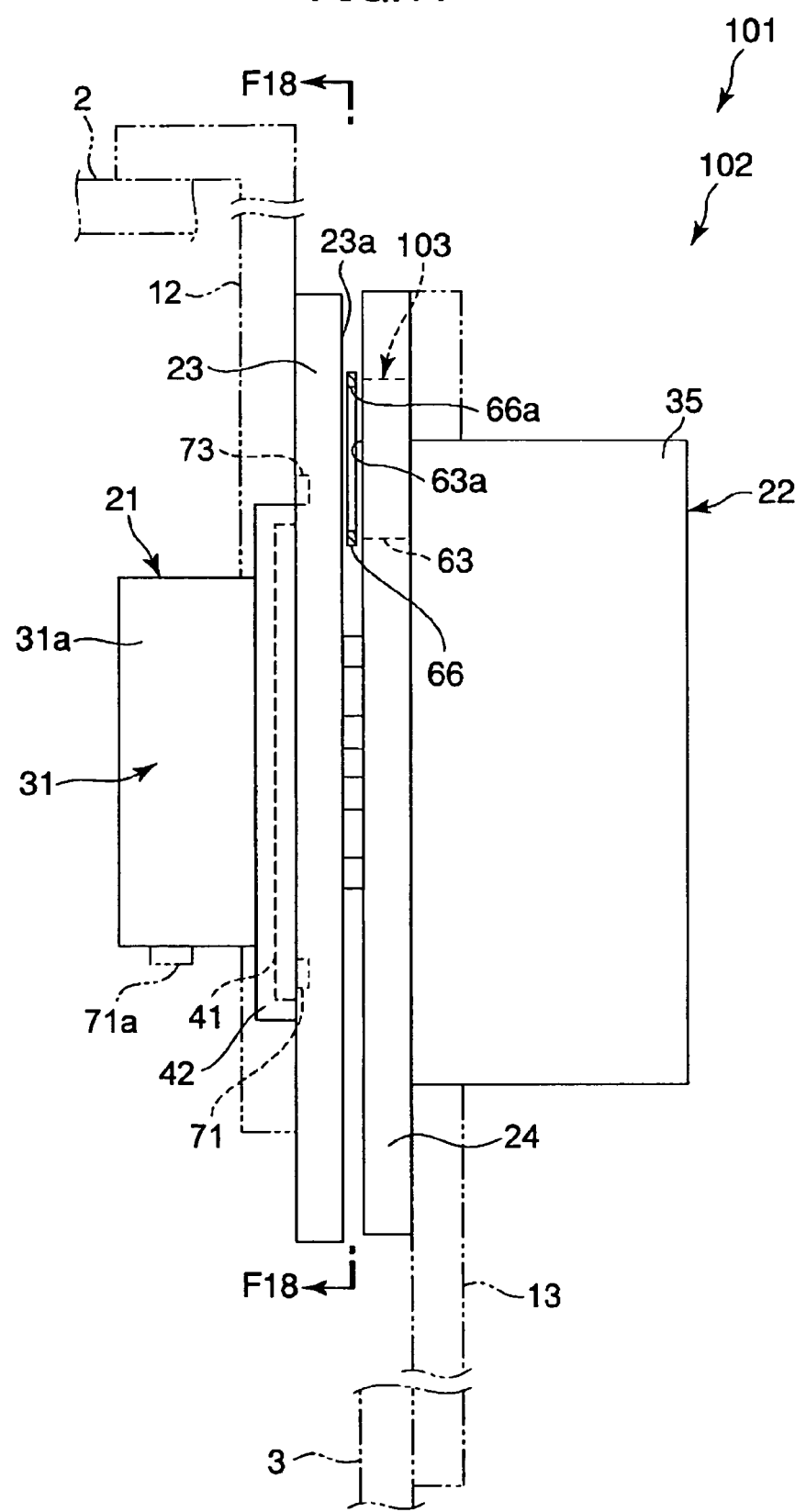
FIG. 17 shows a side view of a drive unit of a wearable motion assistive device according to a third embodiment of the present invention.

The position detecting unit 63 may be attached to the second flange member 24 as shown in FIG. 17, opposite the fluorescent band 69. The position detecting unit 63 has a one-dimensional detection line lying in the radial direction of the first flange member 23. The position detecting unit 63 has a light-receiving surface 63a. The position detecting unit 63 detects a location of the fluorescent band 69 (i.e., position information about the fluorescent band 69 in the radial direction of the first flange member 23) in an area opposite the light-receiving surface 63a.

Based on information about the shape of the spiral of the fluorescent band 69, or with reference to the position information about the fluorescent band 69 at the reference position (rotation angle 0°, the angle calculating unit 64 calculates a relative rotation angle between the first and second flange members 23 and 24 from the detected position information about the fluorescent band 69.

The slit member 66 is provided between the position detecting unit 63 and the first flange member 23. The slit member 66, which is stationary relative to the position detecting unit 63, includes a slit 66a lying in a radius direction of the first flange member 23. The slit member 66 is not necessarily required.

In accordance with the wearable motion assistive device 101 or the drive unit 102 described above, the influence of the scattering of light in the rotation angle detecting unit 103 can be curbed, whereby rotation angle detection accuracy can be improved. Namely, because the fluorescent band 69 emits light by itself, the problem of diffuse reflection of light at the edge of the fluorescent band 69 is not caused, so that light with controlled scattering becomes incident on the position detecting unit 63. As a result, the fluorescent band 69 prevents the error due to the scattering of light, thereby improving the rotation angle detection accuracy. In another embodiment, the fluorescent band 69 may be provided on the second flange member 24 and the position detecting unit 63 may be provided on the first flange member 23.

Figure 19:
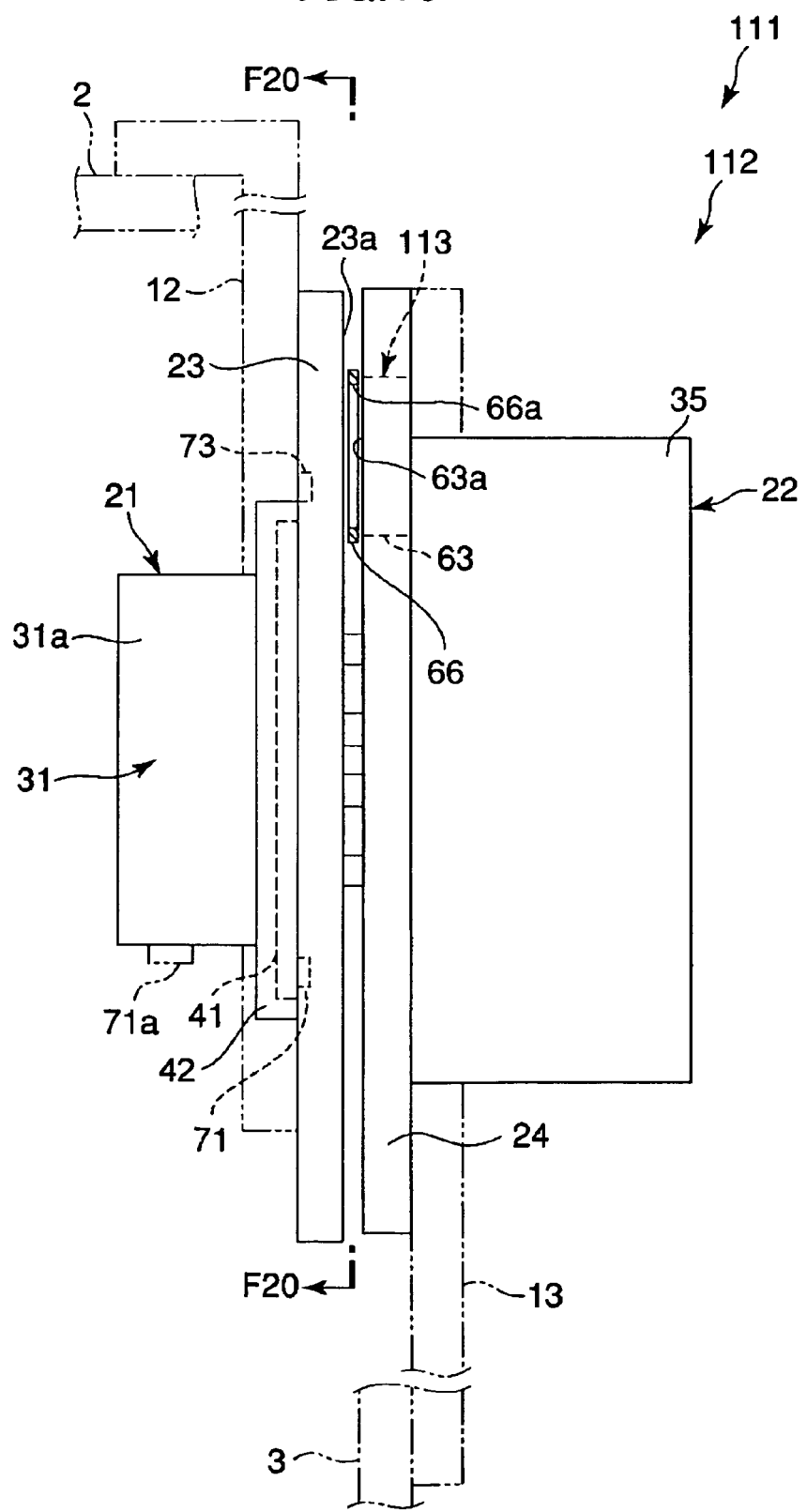
FIG. 19 shows a side view of a drive unit of a wearable motion assistive device according to a fourth embodiment of the present invention.

Hereafter, a wearable motion assistive device 111 according to a fourth embodiment of the present invention is described with reference to FIGS. 19 and 20. Parts or elements with the same functions as those of the wearable motion assistive device 1, 91, or 101 according to the first, second, or third embodiment are designated with similar reference numerals, and their description is omitted.

The wearable motion assistive device 111 includes a shoulder joint mechanism 5 and an elbow joint mechanism 6, each having a drive unit 112. The drive unit 112 is similar to the drive unit of the first embodiment with the exception of a rotation angle detecting unit 113 that differs in structure from the rotation angle detecting unit 51 according to the first embodiment.

The rotation angle detecting unit 113 includes a reflecting band 97, a first light-emitting portion 95, a second light-emitting portion 96, a position detecting unit 63, an angle calculating unit 64, a controller 65, and a slit member 66.

Figure 20:
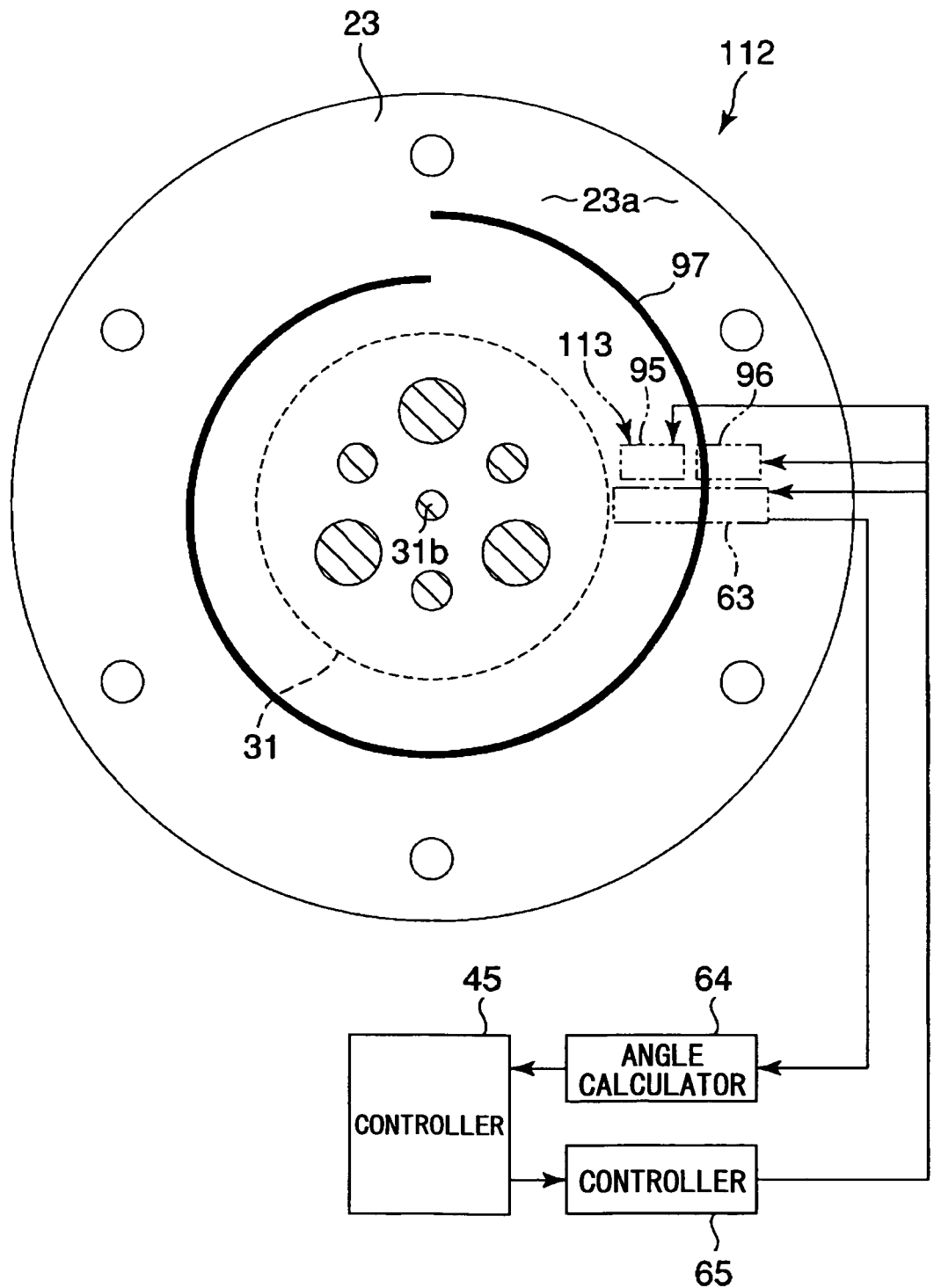
FIG. 20 shows a cross section of the drive unit taken along line F20-F20 of FIG. 19.

As shown in FIG. 20, the reflecting band 97 is installed on an end face 23a of the first flange member 23, opposite the second flange member 24 and extending spirally. Namely, the reflecting band 97 extends such that its position changes in a direction perpendicular to the direction of rotation of the second flange member 24 (i.e., in a radius direction of the first flange member 23 in the present embodiment) as the second flange member 24 is rotated (in a circumferential direction).

The first and second light-emitting portions 95 and 96 may be fixed to the second flange member 24. The first and second light-emitting portions 95 and 96 are spaced apart from each other in the radius direction of the second flange member 24. The first and second light-emitting portions 95 and 96 may be turned on alternately.

The position detecting unit 63 may be attached to the second flange member 24 opposite the reflecting band 97, as shown in FIG. 20. The position detecting unit 63 has a one-dimensional detection line lying in a radius direction of the first flange member 23. For example, the position detecting unit 63 detects the position of a peak ("first peak") in a reflected light distribution detected when the first light-emitting portion 95 is turned on, and the position of a peak ("second peak") of a reflected light distribution detected when the second light-emitting portion 96 is turned on, as in the second embodiment. The position detecting unit 63 may then determine an intermediate position between the first and second peaks as the instantaneous position information about the reflecting band 97. The position detecting unit 63 may employ other detection method.

Based on information about the shape of the spiral of the reflecting band 97 or the position information about the reflecting band 97 at the reference position (rotation angle 0°, the angle calculating unit 64 calculates a relative rotation angle between the first flange member 23 and the second flange member from the detected position information about the reflecting band 97.

The slit member 66 is disposed between the position detecting unit 63 and the first flange member 23. The slit member 66, which includes a slit 66a lying along a radius direction of the first flange member 23, is stationary relative to the position detecting unit 63. The slit member 66 is not necessarily required.

In the wearable motion assistive device 111 or the drive unit 112 described above, the influence of the scattering of light in the rotation angle detecting unit 113 is curbed, whereby improved rotation angle detection accuracy can be obtained. Namely, in the rotation angle detecting unit 113 according to the present embodiment, position information about the reflecting band 97 is detected based on the two reflected light distributions having different scattering characteristics. In this way, the influence of scattering in the individual light distribution on a detection result can be reduced, whereby improved rotation angle detection accuracy can be obtained. The reflecting band 97 may be provided on the second flange member 24 while the position detecting unit 63 may be installed on the first flange member 23.

Figure 21:
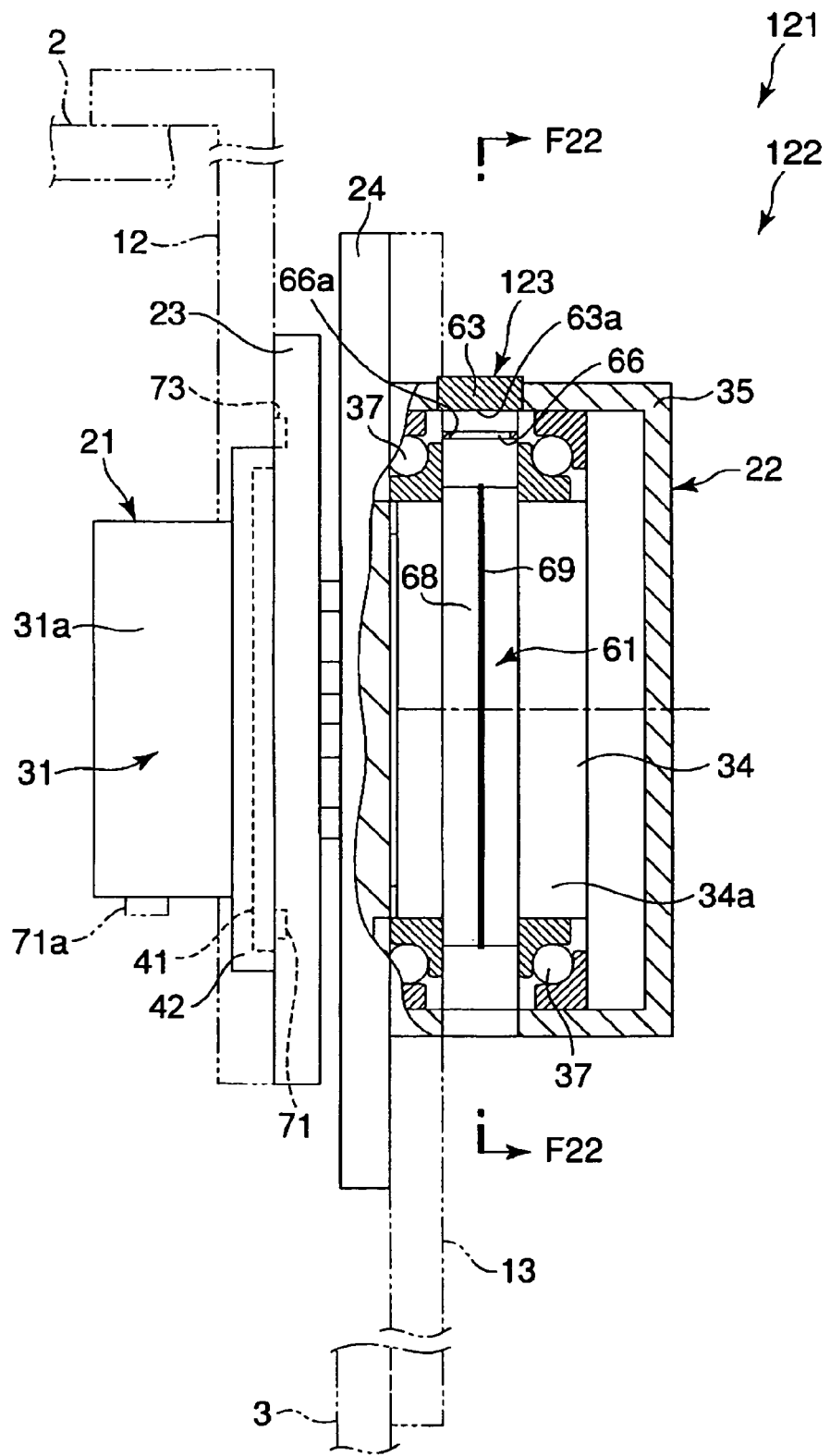
FIG. 21 shows a partially cross-sectional side view of a drive unit of a wearable motion assistive device according to a fifth embodiment of the present invention.

Hereafter, a wearable motion assistive device 121 according to a fifth embodiment of the present invention is described with reference to FIGS. 21 and 22. Parts or elements having the identical or corresponding functions to those of the wearable motion assistive device 1 according to the first embodiment are designated by similar reference numerals, and their description is omitted.

The wearable motion assistive device 121 includes a shoulder joint mechanism 5 and an elbow joint mechanism 6, each having a drive unit 122. The drive unit 122 is similar to the drive unit of the first embodiment with the exception of a rotation angle detecting unit 123 that differs in structure from the rotation angle detecting unit 51 of the first embodiment.

The rotation angle detecting unit 123 includes a detected member 61 with a fluorescent band 69, a light-emitting portion 62, a position detecting unit 63, an angle calculating unit 64, a controller 65, and a slit member 66. In accordance with the present embodiment, the inner case 34 is an example of what the present invention refers to as the first component; the outer case 35 is an example of the second component.

Figure 22:
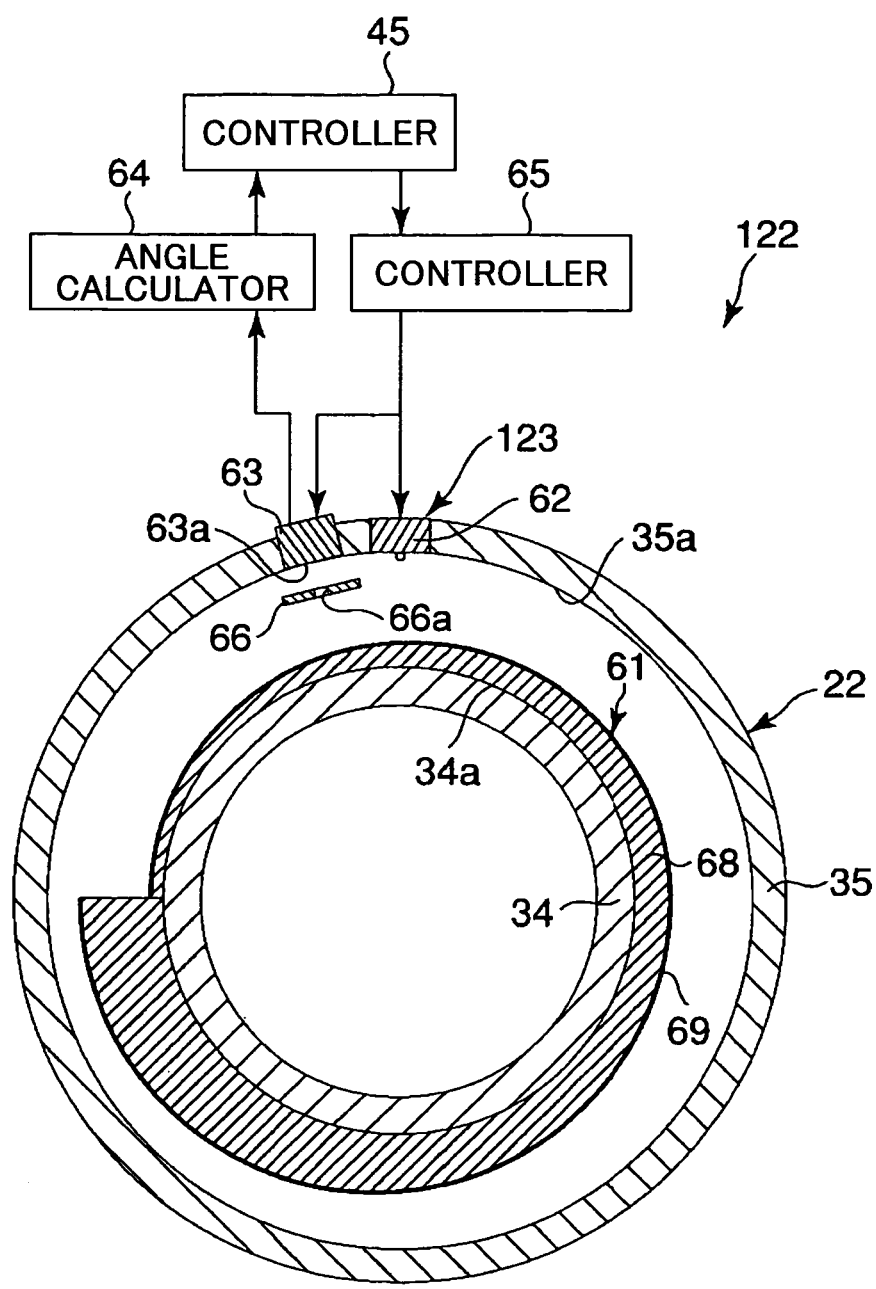
FIG. 22 shows a cross section of the drive unit taken along line F22-F22 of FIG. 21.

As shown in FIG. 22, the detected member 61 includes a main body 68 whose thickness gradually increases in a circumferential direction of the inner case 34. The fluorescent band 69 is provided on the surface of the main body 68. Specifically, the fluorescent band 69 extends along a direction of rotation of the inner case 34 (i.e., circumferential direction) such that the position of the fluorescent band 69 changes in a direction (which is in a radius direction of the inner case 34 in the present embodiment) perpendicular to the direction of rotation of the inner case 34 as the inner case 34 is rotated. Thus, as the inner case 34 and the outer case 35 rotate relative to each other, the position of the fluorescent band 69 changes in the radius direction of the inner case 34.

The light-emitting portion 62 may be fixed to the second flange member 24. The light-emitting portion 62 is turned on and off alternately so that the fluorescent band 69 is irradiated with light intermittently.

The position detecting unit 63 may be attached to the outer case 35 as shown in FIG. 17, opposite the fluorescent band 69. The position detecting unit 63 is configured to detect the amount of light that is incident on the light-receiving surface 63a. Based on the amount of light incident on the light-receiving surface 63a, the position detecting unit 63 detects the location of the fluorescent band 69 (i.e., position information about the fluorescent band 69 in the radius direction of the inner case 34) within an area opposite the light-receiving surface 63a.

Based on the information about the change in thickness of the detected member 61 or the position information about the fluorescent band 69 at the reference position (rotation angle 0°, for example, the angle calculating unit 64 calculates a relative rotation angle between the outer case 35 and the inner case 34 from the detected position information about the fluorescent band 69.

In the wearable motion assistive device 121 or the drive unit 122 described above, the influence of the scattering of light in the rotation angle detecting unit 123 can be curbed, so that improved rotation angle detection accuracy can be obtained. Namely, because the fluorescent band 69 emits light by itself, the problem of diffuse reflection in areas in front and the rear of the fluorescent band 69 does not occur, whereby improved rotation angle detection accuracy can be obtained. The detected member 61 may be provided on the outer case 35 while the position detecting unit 63 may be provided on the inner case 34.

Figure 23:
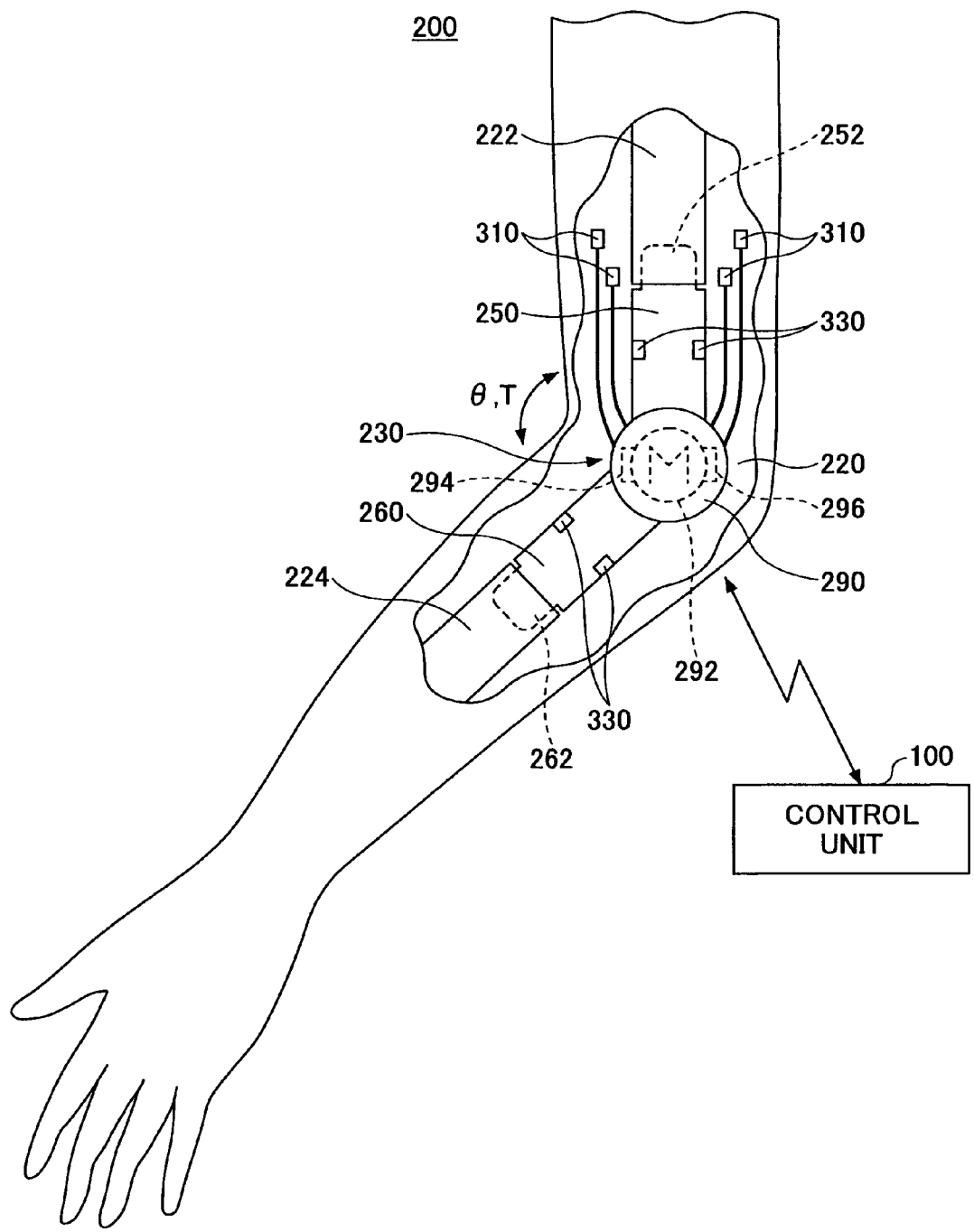
FIG. 23 shows a side view of an embedded motion assistive device 200 according to a sixth embodiment of the present invention.

Hereafter, an embedded motion assistive device 200 according to a sixth embodiment of the present invention is described. FIG. 23 shows a side view of the embedded motion assistive device 200 according to the sixth embodiment.

As shown in FIG. 23, the embedded motion assistive device 200, which is configured to aid the movement of a joint 220 of a wearer, includes a movement aiding unit 230 attached to the joint 220, and a control unit 100. The control unit 100 includes a control circuit for controlling the movement aiding unit 230 externally by radio.

The movement aiding unit 230 includes a first limb 250 coupled to a first bone 222 that is the upper arm bone of the elbow joint 220; a second limb 260 coupled to a second bone 224 that includes the radius on the thumb side and the ulna on the little finger side below the elbow joint 220; and a drive unit 290 disposed between the first limb 250 and the second limb 260 and configured to drive the second limb 260 relative to the first limb 250 in a direction of rotation of the joint. From the upper end of the first limb 250 protrudes a coupling portion 252 connected to the first bone 222. From the lower end of the second limb 260 protrudes a coupling portion 262 connected to the second bone 224.

The coupling portions 252 and 262 of the first limb 250 and the second limb 60 may be made of a corrosion-resistant material, such as titanium, a titanium alloy, or ceramics as these coupling portions 252 and 262 are directly attached to the bones. The coupling portions 252 and 262 may be connected to the bones by using a fastening member, such as screws or rivets, made of a corrosion resistant material such as titanium, a titanium alloy, or ceramics.

On a side surface of the drive unit 290, there are provided a radio transceiver and a control unit. The radio transceiver is configured to transmit a drive information signal to the outside of the body and to receive a control signal from the outside. The control unit is configured to supply a drive current to the drive unit 290.

The drive unit 290 also includes a motor 292 which may be a DC motor, an AC motor, or an ultrasonic motor. The motor 292 is made up of a stator and a rotor, either one consisting of a coil while the other consisting of a permanent magnet. A driving force generated by a relative rotation between the stator and the rotor of the motor 292 is transmitted to the second limb 260 via a reduction mechanism, such as one comprising reduction gears.

The controller 45 of the drive unit 290 generates a drive current that is supplied to the coil of the motor 292, whereby the second limb 260 is rotated relative to the first limb 250.

To the controller 45 of the drive unit 290, there is connected a biopotential sensor 310 for detecting a biopotential in the upper arm. When the wearer attempts to move the arm, a biopotential signal is produced that may include a neurotransmission signal or a myopotential signal. Because the biopotential sensor 310 is embedded in the muscles of the upper arm, the biopotential signal can be detected directly without the intermediary of the skin. Thus, the biopotential signal can be detected more accurately than when the sensor is affixed to the upper surface of the skin of the upper arm.

A rechargeable battery unit 320 is housed within each of the first limb 250 and the second limb 260. The rechargeable battery unit 320 includes a rechargeable battery 324 and a charger unit 322 for charging the rechargeable battery 324 from the outside via electromagnetic induction. A pair of such rechargeable battery units 320 is provided in each limb, one being a main power supply and the other being a standby power supply. Thus, in the movement aiding unit 230, when the voltage of one of the rechargeable batteries 324 decreases, the other rechargeable battery 324 is automatically switched on, thereby preventing a sudden stop. Furthermore, because the rechargeable battery units 320 can be charged while attached inside the body, they can be used for a long time until their chargeable life ends (i.e., within their possible number of times of recharges) while attached to the wearer. The rechargeable battery unit 320 may be provided for each of the first limb 250 and the second limb 260. Alternatively, the rechargeable battery unit 320 may be provided inside either one of the limbs 250 and 260.

The drive unit 290 also includes a torque sensor (physical quantity sensor) 294 for detecting a torque T generated with the supplied drive current, and an angle sensor (physical quantity sensor) 296 for detecting a rotation angle θ between the first limb 250 and the second limb 260. The torque sensor 294 and the angle sensor 296 output torque and angle detection signals to the drive unit 290. The torque sensor 294 may comprise a magnetorestrictive torque sensor configured to detect a distortion in a shaft transmitting a rotary driving force, or an electromagnetic torque sensor configured to detect a phase difference between a drive-side gear and a load-side gear of the motor 292 electromagnetically. The angle sensor 296 may comprise a rotary encoder configured to output a number of pulses corresponding to a rotation angle, or a potentiometer whose resistance value varies depending on the rotation angle.

On the outside of the first limb 250 and the second limb 260, there are provided stress sensors (physical quantity sensors) 330 for detecting a stress (strain) that is caused when the motor is driven. The stress sensor 330 may comprise a strain gauge configured to output a detection signal corresponding to the stress applied to the first limb 250 or the second limb 260 to the controller 45 of the drive unit 290.

The controller 45 transmits the individual detection signals received from the torque sensor 294, the angle sensor 296, the biopotential sensor 310, and the stress sensor 330 to the control unit 100 via the radio transceiver. The control unit 100 then transmits information about the operating status of the drive unit 290 obtained from the controller 45 to the information management apparatus 84 at the center via the communication network 83.

The information management apparatus stores the received information about the operating status of the drive unit 290 in the database 88 for analysis by the analyzing unit 87. An analysis result is sent to the control unit 100 via the communication network 83. Depending on the operational status of the drive unit 290, the control unit 100 relaxes (reduces) the motor torque or the rotation angle in order to prevent an overload state.

The aforementioned radio transceiver 280, the motor 292, the torque sensor 294, and the angle sensor 296 are housed within the case of the drive unit 290. The drive unit 290 installed within the joint 220 has a water-proof structure to prevent the body fluid from entering inside the case and causing malfunction of the motor 292. The control process in the embedded motion assistive device 200 is similar to the sequence described with reference to the flowcharts described above, and is therefore not described.

In another embodiment, the drive unit 290 may include the control unit 100 so that the drive unit 290 can transmit the operating status information directly to the information management apparatus 84 at the center.

Hereafter, an embedded motion assistive device 500 according to a seventh embodiment is described.

Figure 24:
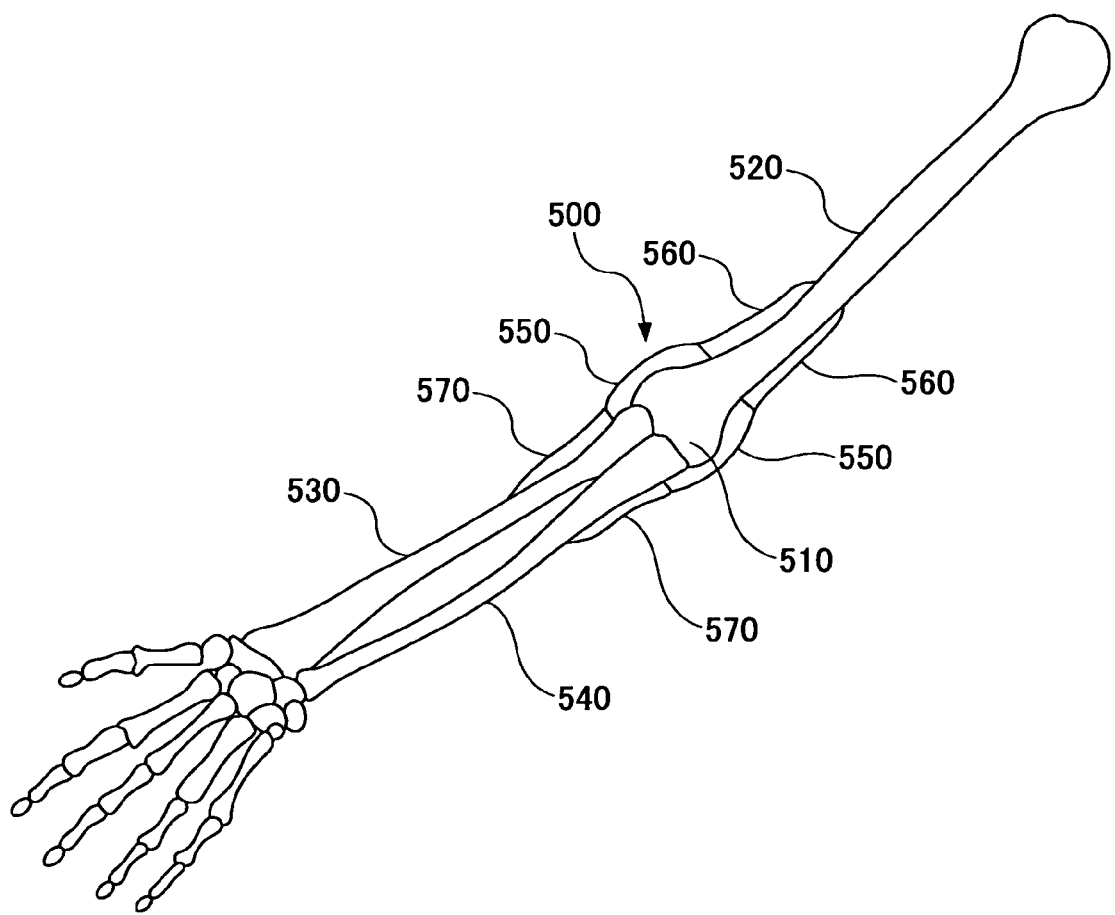
FIG. 24 shows a perspective view of an embedded motion assistive device 500 according to a seventh embodiment of the present invention.

FIG. 24 shows a perspective view of the embedded motion assistive device 500. As shown, the embedded motion assistive device 500 is attached on the outside of the joint 510. A drive unit 550 is closely attached to each of the left and right sides of the joint 510 where the upper arm bone 520 is connected to the radius 530 and the ulna 540. The drive unit 550 includes a thin motor housed within the water-proof structure case. The inside of the drive unit 550 is curved to conform to the shape of the joint 510, and is formed of a low-friction material with a small friction coefficient for reduced friction with the joint 510.

A first limb 560 is coupled to the upper part of the drive unit 550 and is fixed to the upper arm bone 520 via a fastening member. The first limb 560 houses a thin, electromagnetic charger unit and a thin rechargeable battery. At the upper part of the drive unit 550, there is connected a second limb 570 that is fixed to the radius 530 and the ulna 540 via a fastening member. The second limb 570 also houses a thin, electromagnetic charger unit and a thin rechargeable battery.

The drive unit 550 is controlled by the control unit 100 via a radio signal, as in the foregoing embodiment. A control process in the embedded motion assistive device 500 is similar to the sequence shown in the flowcharts described above and is therefore not described.

Thus, in the present embodiment, the embedded motion assistive device 500 is attached externally to the joint 510 by reducing the size of the drive units 550, the first limbs 560, and the second limbs 570. Accordingly, the motion assistive device can be concealed from the outside and does not require attaching/detaching operations, thus providing an enhanced user-friendliness to people with disabled arms or legs.

The drive unit 550 also transmits operating status information to the information management apparatus 84 at the center described above, via the communication network 83.

The information management apparatus 84 then stores the received operating status information about the drive unit 550 in the database 88 for analysis by the analyzing unit 87. An analysis result is then sent to the control unit 100 via the communication network 83. Based on the operational status of the drive unit 550, the control unit 100 relaxes (reduces) the motor torque or the rotation angle in order to prevent an overload state.

In another embodiment, the drive unit 550 may include the control unit 100 so that the drive unit 550 can transmit the operating status information to the central information management apparatus 84 directly.

In the foregoing, the wearable motion assistive devices 1, 91, 101, 111, and 121, and the embedded motion assistive devices 200 and 500 according to the first through seventh embodiments have been described. Also, the drive units 11, 92, 102, 112, 122, 290, and 550 according to the first and second embodiments have been described. These, however, are merely examples of the present invention, and it goes without saying that the present invention is not limited by any of the foregoing embodiments.

The present application is based on the Japanese Priority Applications No. 2006-272223 filed Oct. 3, 2006, and No. 2007-242648 filed Sep. 19, 2007, the entire contents of which are hereby incorporated by reference.

The invention claimed is:

1. A motion assistive device comprising a drive unit configured to aid or execute an operation of a joint, and a control unit configured to control the drive unit,
    the drive unit including:
        a motor configured to provide an inputted driving force; and
        a circuit board on which a controller is mounted, the controller producing a drive signal supplied to the motor based on a control signal sent from the control unit,
    wherein the controller includes:
        a motor monitoring unit configured to monitor an operational status of the motor; and a motor control unit configured to limit the drive signal supplied to the motor based on a result of monitoring by the motor monitoring unit in order to prevent an overload state of the motor;

wherein the drive unit further includes:

a case housing the motor;

a rotating body housed within the case and having a circumferential surface that rotates relative to the case when the motor is driven;

a fluorescent band disposed on and extending along the circumferential surface of the rotating body while inclined with respect to a circumferential direction of the rotating body;

a light-emitting portion configured to irradiate the fluorescent band with light;

a detecting unit that remains stationary relative to the case and includes a light-receiving surface opposite the fluorescent band, the detecting unit being configured to detect position information about the fluorescent band in an axial direction of the rotating body by receiving light emitted by the fluorescent band; and a calculating unit configured to calculate a relative rotation angle between the case and the rotating body based on the position information about the fluorescent band detected by the detecting unit.

2. The motion assistive device according to claim 1, further comprising:

a physical quantity detecting unit configured to detect a physical quantity concerning the operation of the joint; and a biosignal detecting unit configured to detect a biosignal that is generated when the joint is moved, wherein the control unit controls the drive unit based on the physical quantity detected by the physical quantity detecting unit and the biosignal detected by the biosignal detecting unit.

3. The motion assistive device according to claim 1, wherein the motor control unit includes:

a determination unit configured to determine whether a total integrated value of electric current inputted to the motor exceeds a preset threshold;

and wherein the motor control unit is configured to decrease the drive signal supplied to the motor gradually at a predetermined rate when the determination unit determines that the total integrated value of the electric current exceeds the preset threshold.

4. The motion assistive device according to claim 1, wherein the motor control unit includes:

a determination unit configured to determine whether a temperature of the circuit board exceeds a preset threshold;

and wherein the motor control unit gradually decreases the drive signal supplied to the motor at a predetermined rate when the determination unit determines that the temperature of the circuit board exceeds the preset threshold.

5. The motion assistive device according to claim 1, wherein the motor control unit includes:

a determination unit configured to determine whether a temperature of the motor exceeds a preset threshold;

and wherein the motor control unit gradually decreases the drive signal supplied to the motor at a predetermined rate when the determination unit determines that the temperature of the motor exceeds the preset threshold.

6. A motion assistive device comprising a drive unit configured to aid or execute an operation of a joint, and a control unit configured to control the drive unit, the drive unit including:

a motor configured to provide an inputted driving force; and a controller configured to produce a drive signal supplied to the motor based on a control signal sent from the control unit, wherein the controller includes:

a motor monitoring unit configured to calculate a remaining lifetime of the motor by subtracting a total operation time of the motor from a lifetime of the motor; and a motor control unit configured to gradually decrease the drive signal supplied to the motor at a predetermined rate when the remaining lifetime of the motor calculated by the motor monitoring unit reaches a preset value;

wherein the drive unit further includes:

a case housing the motor;

a rotating body housed within the case and having a circumferential surface that rotates relative to the case when the motor is driven;

a fluorescent band disposed on and extending along the circumferential surface of the rotating body while inclined with respect to a circumferential direction of the rotating body;

a light-emitting portion configured to irradiate the fluorescent band with light;

a detecting unit that remains stationary relative to the case and includes a light-receiving surface opposite the fluorescent band, the detecting unit being configured to detect position information about the fluorescent band in an axial direction of the rotating body by receiving light emitted by the fluorescent band; and a calculating unit configured to calculate a relative rotation angle between the case and the rotating body based on the position information about the fluorescent band detected by the detecting unit.

7. The motion assistive device according to claim 3, wherein the controller includes:

a storage unit configured to store a first acceptable value of the electric current supplied to the motor, and a second acceptable value that is higher than the first acceptable value; and a calculating unit configured to integrate an electric current value in excess of the first acceptable value;

and wherein the motor control unit gradually decreases the value of the electric current supplied to the motor at a predetermined rate when an integrated value calculated by the calculating unit exceeds the threshold.

8. The motion assistive device according to claim 7, wherein the motor control unit is configured to gradually decrease the value of the electric current supplied to the motor to or below the first acceptable value when the value of the electric current supplied to the motor exceeds the second acceptable value.

9. The motion assistive device according to claim 1, wherein the light-emitting portion is configured to turn on and off alternately when irradiating the fluorescent band with light, and the detecting unit is configured to detect the position information about the fluorescent band by receiving light emitted by the fluorescent band when the light-emitting portion is turned off.

10. A motion assistive device comprising a drive unit configured to aid or execute an operation of a joint, and a control unit configured to control the drive unit,
  the drive unit including:
    a motor configured to provide an inputted driving force; and
    a circuit board on which a controller is mounted, the controller producing a drive signal supplied to the motor based on a control signal sent from the control unit,
  wherein the controller includes:
    a motor monitoring unit configured to monitor an operational status of the motor; and
    a motor control unit configured to limit the drive signal supplied to the motor based on a result of monitoring by the motor monitoring unit in order to prevent an overload state of the motor;
  wherein the drive unit further includes:
    a case housing the motor;
    a rotating body housed within the case and having a circumferential surface that rotates relative to the case when the motor is driven;
    a reflecting band disposed on and extending along the circumferential surface of the rotating body while inclined with respect to a circumferential direction of the rotating body,
    a first light-emitting portion configured to irradiate the reflecting band with light;
    a second light-emitting portion disposed away from the first light-emitting portion in an axial direction of the rotating body and configured to irradiate the reflecting band with light;
    a detecting unit that remains stationary relative to the case and includes a light-receiving surface opposite the reflecting band, the detecting unit being configured to detect position information about the reflecting band in the axial direction of the rotating body by receiving light from the first light-emitting portion that is reflected by the reflecting band and light from the second light-emitting portion that is reflected by the reflecting band; and
    a calculating unit configured to calculate a relative rotation angle between the case and the rotating body based on the position information about the reflecting band detected by the detecting unit.

11. The motion assistive device according to claim 10, wherein the first light-emitting portion and the second light-emitting portion are configured to turn on alternately, and
  the detecting unit detects the position information about the reflecting band based on a distribution of reflected light that is detected when the first light-emitting portion is turned on and a distribution of reflected light that is detected when the second light-emitting portion is turned on.

12. The motion assistive device according to claim 1, wherein the rotating body comprises a gear case in which one or plural gears are housed.

13. The motion assistive device according to claim 12, including a slit member disposed between the detecting unit and the rotating body and having a slit formed in the axial direction of the rotating body.

14. A maintenance management system for a motion assistive device, the maintenance management system comprising:
  a motion assistive device comprising a drive unit configured to aid or execute an operation of a joint, and a control unit configured to control the drive unit;
  the drive unit including:
    a motor configured to provide an inputted driving force; and
    a circuit board on which a controller is mounted, the controller producing a drive signal supplied to the motor based on a control signal sent from the control unit,
  wherein the controller includes:
    a motor monitoring unit configured to monitor an operational status of the motor; and
    a motor control unit configured to limit the drive signal supplied to the motor based on a result of monitoring by the motor monitoring unit in order to prevent an overload state of the motor;
  wherein the drive unit further includes:
    a case housing the motor;
    a rotating body housed within the case and having a circumferential surface that rotates relative to the case when the motor is driven; and
    a communication unit configured to transmit information including history information about a drive status of the motor;
    a fluorescent band disposed on and extending along the circumferential surface of the rotating body while inclined with respect to a circumferential direction of the rotating body;
    a light-emitting portion configured to irradiate the fluorescent band with light;
    a detecting unit that remains stationary relative to the case and includes a light-receiving surface opposite the fluorescent band, the detecting unit being configured to detect position information about the fluorescent band in an axial direction of the rotating body by receiving light emitted by the fluorescent band; and
    a calculating unit configured to calculate a relative rotation angle between the case and the rotating body based on the position information about the fluorescent band detected by the detecting unit;
  wherein the maintenance management system further comprises:
    a receiver unit provided at a center for managing an operational status of the motion assistive device and configured to receive the history information about the drive status of the motor that the drive unit transmits via the communication unit and a communication network;
    a database configured to store the history information about the drive status of the motor that is inputted via the receiver unit;
    an analyzing unit configured to generate information about a lifetime of the drive unit or a presence or an absence of an overload state in the drive unit by analyzing the history information stored in the database; and
    a transmitter unit configured to transmit maintenance information to the drive unit when it is determined that the motor needs maintenance based on a result of analysis by the analyzing unit.

15. The motion assistive device according to claim 6, wherein the light-emitting portion is configured to turn on and off alternately when irradiating the fluorescent band with light, and
  the detecting unit is configured to detect the position information about the fluorescent band by receiving light emitted by the fluorescent band when the light-emitting portion is turned off.

16. A motion assistive device comprising a drive unit configured to aid or execute an operation of a joint, and a control unit configured to control the drive unit, the drive unit including:
- a motor configured to provide an inputted driving force; and
- a controller configured to produce a drive signal supplied to the motor based on a control signal sent from the control unit, wherein the controller includes:
- a motor monitoring unit configured to calculate a remaining lifetime of the motor by subtracting a total operation time of the motor from a lifetime of the motor; and
- a motor control unit configured to gradually decrease the drive signal supplied to the motor at a predetermined rate when the remaining lifetime of the motor calculated by the motor monitoring unit reaches a preset value;

wherein the drive unit further includes:
- a case housing the motor;
- a rotating body housed within the case and having a circumferential surface that rotates relative to the case when the motor is driven;
- a reflecting band disposed on and extending along the circumferential surface of the rotating body while inclined with respect to a circumferential direction of the rotating body,
- a first light-emitting portion configured to irradiate the reflecting band with light;
- a second light-emitting portion disposed away from the first light-emitting portion in an axial direction of the rotating body and configured to irradiate the reflecting band with light;
- a detecting unit that remains stationary relative to the case and includes a light-receiving surface opposite the reflecting band, the detecting unit being configured to detect position information about the reflecting band in the axial direction of the rotating body by receiving light from the first light-emitting portion that is reflected by the reflecting band and light from the second light-emitting portion that is reflected by the reflecting band; and
- a calculating unit configured to calculate a relative rotation angle between the case and the rotating body based on the position information about the reflecting band detected by the detecting unit.

17. The motion assistive device according to claim 6, wherein the drive unit includes a communication unit configured to transmit information including history information about a drive status of the motor.

* * * * *